US011708372B2

(12) United States Patent
Reddy et al.

(10) Patent No.: US 11,708,372 B2
(45) Date of Patent: Jul. 25, 2023

(54) CRYSTALLINE COMPOSITION OF TILDACERFONT AND METHODS OF USE AND PREPARATION THEREOF

(71) Applicant: Spruce Biosciences, Inc., Daly City, CA (US)

(72) Inventors: Dasharatha Reddy, San Ramon, CA (US); Ashokraj Rajagopal, Alameda, CA (US); Lu Wang, Berkeley, CA (US); Christopher Barnes, San Francisco, CA (US)

(73) Assignee: SPRUCE BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 17/720,074

(22) Filed: Apr. 13, 2022

(65) Prior Publication Data
US 2023/0159533 A1     May 25, 2023

Related U.S. Application Data

(60) Provisional application No. 63/281,462, filed on Nov. 19, 2021.

(51) Int. Cl.
  C07D 487/04      (2006.01)
(52) U.S. Cl.
  CPC ........ C07D 487/04 (2013.01); C07B 2200/13 (2013.01)
(58) Field of Classification Search
  CPC .................................................. C07D 487/04
  See application file for complete search history.

(56) References Cited

U.S. PATENT DOCUMENTS

| | | | |
|---|---|---|---|
| 8,030,304 | B2 | 10/2011 | Chen et al. |
| 8,563,718 | B2 | 10/2013 | Rizzo et al. |
| 10,849,908 | B2 | 12/2020 | Howerton et al. |
| 11,007,201 | B2 | 5/2021 | Howerton et al. |
| 11,311,549 | B2 | 4/2022 | Howerton et al. |
| 11,344,557 | B2 | 5/2022 | Howerton et al. |
| 11,351,177 | B2 | 6/2022 | Howerton et al. |
| 2002/0013357 | A1 | 1/2002 | Nadkarni et al. |
| 2003/0008885 | A1 | 1/2003 | He et al. |
| 2006/0078623 | A1 | 4/2006 | Dhoot et al. |
| 2009/0076266 | A1 | 3/2009 | Daugulis et al. |
| 2010/0022560 | A1 | 1/2010 | Chen et al. |
| 2010/0155595 | A1 | 6/2010 | Ghoshal et al. |
| 2013/0045979 | A1 | 2/2013 | Sanfilippo |
| 2017/0020877 | A1 | 1/2017 | Grigoriadis |
| 2017/0333126 | A1 | 11/2017 | Sobotka |
| 2018/0110554 | A1 | 4/2018 | Zarins et al. |
| 2020/0255436 | A1 | 8/2020 | Howerton et al. |
| 2021/0015827 | A1 | 1/2021 | Howerton et al. |
| 2021/0038604 | A1* | 2/2021 | Howerton ............... A61P 35/00 |
| 2021/0137935 | A1 | 5/2021 | Howerton et al. |
| 2021/0322430 | A1 | 10/2021 | Howerton et al. |
| 2021/0361664 | A1 | 11/2021 | Howerton et al. |
| 2022/0143037 | A1 | 5/2022 | Howerton et al. |

FOREIGN PATENT DOCUMENTS

| | | |
|---|---|---|
| EP | 2094709 B1 | 9/2010 |
| JP | 2000503661 A | 3/2000 |
| JP | 2000302693 A | 10/2000 |
| JP | 2002501922 A | 1/2002 |
| JP | 2002513382 A | 5/2002 |
| JP | 2008533201 A | 8/2008 |
| JP | 2010504344 A | 2/2010 |
| JP | 2012504626 A | 2/2012 |
| JP | 2017503030 A | 1/2017 |
| WO | WO-9413676 A1 | 6/1994 |

(Continued)

OTHER PUBLICATIONS

Bornstein et al. Diagnosis and Treatment of Primary Adrenal Insufficiency: An Endocrine Society Clinical Practice Guideline. J Clin Endocrinol Metab 101(2):364-389 (2016).
Chen et al. Design of 2,5-Dimethyl-3-(6-dimethyl-4-methylpyridin-3-yl)-7-dipropyl aminopryazolo[1,5-a]pyrimidine (NBI 30775/R121919) and Structure-Activity Relationships of a Series of Potent and Orally Active Corticotropin—Releasing Factor Receptor Antagonists. J. O Medicinal Chemistry Society 47(19) 4787-4798 XP001206057 (2004).
Co-pending U.S. Appl. No. 18/078,649, inventors Howerton; Alexis et al., filed on Dec. 9, 2022.
Dave. Overview of pharmaceutical excipients used in tablets and capsules. https://www.drugtopics.com/view/overview-pharmaceutical-excipients-used-tablets-and-capsules (Oct. 24, 2008).
EP18846043.0 Extended Search Report dated Feb. 10, 2021.

(Continued)

*Primary Examiner* — Brian E McDowell
(74) *Attorney, Agent, or Firm* — Wilson Sonsini Goodrich & Rosati

(57) ABSTRACT

Described herein are crystalline composition comprising a Corticotropin-releasing hormone receptor 1 (CRF1) antagonist, such as Compound 1:

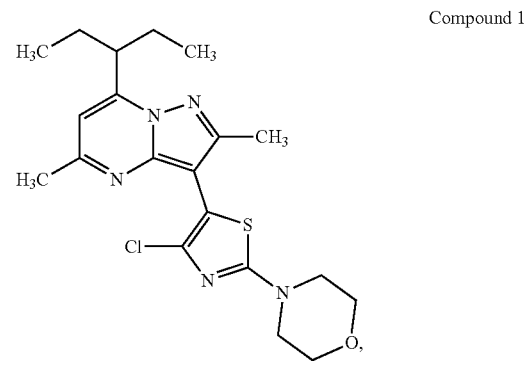

methods of making such crystalline composition, pharmaceutical compositions and medicaments comprising such crystalline composition, and methods of using such crystalline composition in the treatment of conditions, diseases, or disorders that would benefit from modulation of CRF.

12 Claims, 7 Drawing Sheets

(56) References Cited

FOREIGN PATENT DOCUMENTS

| WO | WO-9729109 A1 | 8/1997 |
|---|---|---|
| WO | WO-9803510 A1 | 1/1998 |
| WO | WO-9808847 A1 | 3/1998 |
| WO | WO-0059908 A2 | 10/2000 |
| WO | WO-0123388 A2 | 4/2001 |
| WO | WO-02072202 A1 | 9/2002 |
| WO | WO-2005063755 A1 | 7/2005 |
| WO | WO-2006102194 A1 | 9/2006 |
| WO | WO-2008036579 A1 | 3/2008 |
| WO | WO-2010039678 A1 | 4/2010 |
| WO | WO-2015112642 A1 | 7/2015 |
| WO | WO-2019036472 A1 | 2/2019 |
| WO | WO-2019036503 A1 | 2/2019 |
| WO | WO-2022036123 A1 | 2/2022 |

OTHER PUBLICATIONS

EP18846689.0 Extended European Search Report dated Dec. 22, 2020.
Escobar-Morreale, HF., Polycystic ovary syndrome: definition, aetiology, diagnosis and treatment. Nat Rev Endocrinol. 14(5):270-284 (2018).
Fuqua et al. Duration of suppression of adrenal steroids after glucocorticoid administration. Int J Pediatr Endocrinol 2010:712549 (2010).
Gehlert et al. 3-(4-Chloro-2-morpholin-4-yl-thiazol-5-yl )-8-(1-ethylpropyl)-2,6-dimethyl-imidazo[I ,2-b]pyridazine: a novel brain-penetrant, orally available corticotropin-releasing factor receptor 1 antagonist with efficacy in animal models of alcoholism. The Journal of Neuroscience 27(10):2718-2726 (2007).
Gennaro. Remington: The Science and Practice of Pharmacy. 21st Ed. Mack Pub. Co., Easton, PA (2005).
Gilligan P. et al., The Discovery of 4-(3-Pentylamino)-2,7-dimethyl-8-(2-methyl-4-methoxyphenyl)-pyrazolo-[1,5-alpha]-pyrimidine: A corticotrophin-Releasing Factor (hCRF1)Antagonist. Bioorganic & Medicinal Chemistry 181-189 (2000).
He Liqi et al. 4-(1,3-Dimethoxyprop-2-ylamino)-2,7-dimethyl-8-(2,4-dichlorophenyl)pyrazolo[1,5-a]-1,3,5-triazine: A Potent, Orally Bioavailable CRF1 Receptor Antagonist. J. of Medicinal Chem. American Chem. Society. Washington, US, vol. 43, 449-456 XP002196777 (2000).
Hien-Quang Do. A General Method for Copper-Catalyzed Arylation of Arene C-H Bonds. J Am Chem Soc. Nov. 12, 2008; 130(45): 15185-15192.
Hien-Quang Do. Copper-Catalyzed Arylation and Alkenylation of Polyfluoroarene C-H Bonds. Journal of American Chemical Society 2008, 1128-1129.
Hien-Quang Do. Copper-Catalyzed Arylation of Heterocycle C-H Bonds. J Am Chem Soc. Oct. 17, 2007; 129(41): 12404-12405.
Hodgetts et al. Discovery of N-(1-ethylpropyl)-[3-methoxy-5-(2-methoxy-4-trifluoromethoxyphenyl)-6-methyl-pyrazin-2-yl]amine 59 (NGD 98-2): an orally active corticotropin releasing factor-1 (CRF-1) receptor antagonist. J Med Chem 54:4187-4206 (2011).
Khadilkar et al., Can polycystic ovarian syndrome be cured? Unfolding the concept of secondary polycystic ovarian syndrome. J Obstet Gynaecol India 69(4):297-302 (2019).
Lee et al. Attenuated Forms of Congenital Adrenal Hyperplasia due to 21-Hydroxylase Deficiency. J Clin Endocrinol Metab. 55(5):866-871 (1982).
Majo et al. Facile Palladium-Catalyzed Synthesis of 3-Arylpyrazolo-[1,5-a]pyrimidines. Adv. Synth. Catal. 2003, 620-624.
Malvern Instruments Worldwide. A Basic Guide to Particle Characterization. Inform—White Paper. 2012. 26 Pages.
O'Reilly et al., 11-oxygenated C19 steroids are the predominant androgens in polycystic ovary syndrome. J Clin Endocrinol Metab. 102(3):840-848 (2017).
PCT/US2007/078605 Written Opinion dated Mar. 20, 2009.
PCT/US2009/058722 International Search Report dated Apr. 8, 2010.
PCT/US2009/058722 Written Opinion dated Apr. 2, 2011.
PCT/US2018/046707 International Search Report and Written Opinion dated Oct. 24, 2018.
PCT/US2018/046760 International Search Report and Written Opinion dated Oct. 24, 2018.
PCT/US2021/045780 International Search Report and Written Opinion dated Dec. 17, 2021.
PCT/US2022/050436 International Search Report and Written Opinion dated Nov. 18, 2022.
Rosenfield et al., The pathogenesis of polycystic ovary syndrome (PCOS): the hypothesis of PCOS as functional ovarian hyperandrogenism revisited. Endocrine Reviews 37(5):467-520 (2016).
Sarafoglou et al. Tildacerfont in Adults with Classic Congenital Adrenal Hyperplasia: Results from Two Phase 2 Studies. J Clin Endocrinol Metab. Oct. 21, 2021; 106(11):e4666-e4679.
Thakral et al. Salt Disproportionation in the Solid State: Role of Solubility and Counterion Volatility. Mol Pharm 13(12):4141-4151 (2016).
Turcu et al. Single-Dose Study of a Corticotripin-Releasing Factor Receptor-1 Antagonist in Women With 21-Hydroxylase Deficiency. J Clin Endocrinol Metab 101(3):1174-1180 (2016).
U.S. Appl. No. 16/388,620 Notice of Allowance dated Sep. 30, 2020.
U.S. Appl. No. 17/063,592 Notice of Allowance dated Mar. 25, 2022.
U.S. Appl. No. 17/078,054 Notice of Allowance dated Mar. 9, 2021.
U.S. Appl. No. 17/359,414 Notice of Allowance dated Mar. 4, 2022.
U.S. Appl. No. 17/586,228 Office Action dated Jun. 10, 2022.
U.S. Appl. No. 12/377,733 Notice of Allowance dated May 27, 2011.
U.S. Appl. No. 16/388,620 Office Action dated Jul. 15, 2019.
U.S. Appl. No. 16/388,620 Office Action dated Nov. 25, 2019.
U.S. Appl. No. 16/639,540 Office Action dated Jul. 11, 2022.
U.S. Appl. No. 16/639,540 Office Action dated Nov. 16, 2021.
U.S. Appl. No. 17/063,592 Office Action dated Dec. 7, 2021.
U.S. Appl. No. 17/078,054 Office Action dated Dec. 14, 2020.
U.S. Appl. No. 17/359,411 Notice of Allowance dated Apr. 28, 2022.
U.S. Appl. No. 17/359,411 Notice of Allowance dated Apr. 4, 2022.
U.S. Appl. No. 17/359,411 Notice of Allowance dated Mar. 22, 2022.
U.S. Appl. No. 17/359,411 Office Action dated Jan. 6, 2022.
U.S. Appl. No. 17/359,414 Office Action dated Nov. 16, 2021.
Varma. Excipients used in the Formulation of Tablets. https://www.rroij.com/openaccess/excipients-used-in-the-formulationof-tablets-.php?aid=78260 Revised date: Jul. 26, 2016.
Zhang et al. D-Level Essay in Statistics, 2009, How to Analyze Change from Baseline. Available at http://www.statistics.du.se/essays/D09 Zhang%20Ling%20&%20Han%20Kun.pdf (Jun. 10, 2009).

* cited by examiner

CRYSTALLINE COMPOSITION OF TILDACERFONT AND METHODS OF USE AND PREPARATION THEREOF

CROSS-REFERENCE TO RELATED APPLICATIONS

This application claims the benefit of U.S. Provisional Application No. 63/281,462, filed on Nov. 19, 2021, which is incorporated herein by reference in its entirety.

BACKGROUND

Corticotropin releasing factor (CRF) is a 41 amino acid peptide that is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in the brain. There is also evidence that CRF plays a significant role in integrating the response in the immune system to physiological, psychological, and immunological stressors.

SUMMARY OF THE INVENTION

In a first aspect, the present disclosure provides a crystalline composition according to Formula I:

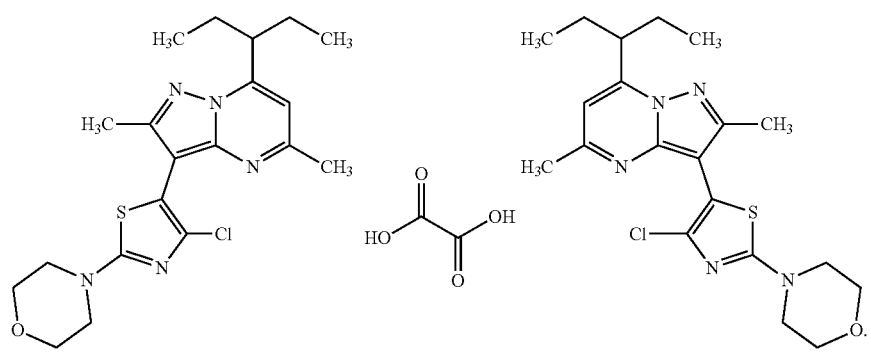

Formula I

In some embodiments, the crystals of the crystalline composition according to Formula I have unit cell parameters at T=150°K of: a=34.003(4) Å, b=6.5843(13) Å, c=21.062(5) Å; β=108.703(12)°, V=4466.5(15) Å$^3$ and a monoclinic C2/c space group.

In some embodiments, the crystals of the crystalline composition according to Formula I is characterized by:
(a) an X-ray powder diffraction pattern comprising peaks at 10.84±0.2° 2-θ, 15.96±0.2° 2-θ, 23.44±0.2° 2-θ, and 24.80±0.2° 2-θ, and as measured by X-ray powder diffraction using an X-ray wavelength of 0.71073 Å;
(b) an X-ray powder diffraction pattern substantially the same as shown in FIG. 1;
(c) a differential scanning calorimetry (DSC) thermogram comprising an endotherm in the range of about 160° C. to 170° C.;
(d) a differential scanning calorimetry (DSC) thermogram comprising an endotherm with an onset of about 164° C. and a peak of about 166° C.;
(e) a differential scanning calorimetry (DSC) thermogram substantially the same as shown in FIG. 2;
(f) a thermogravimetric analysis (TGA) thermogram comprising a loss in mass of about 11% over a temperature range of about 25° C. to about 200° C.;
(g) a thermogravimetric analysis (TGA) thermogram substantially the same as shown in FIG. 3; or
(h) combinations thereof.

In some embodiments, the crystalline composition according to Formula I is characterized by an X-ray powder diffraction pattern comprising peaks at 10.84±0.2° 2-θ, 15.96±0.2° 2-θ, 23.44±0.2° 2-θ, and 24.80±0.2° 2-θ, and as measured by X-ray powder diffraction using an X-ray wavelength of 0.71073 Å. In some embodiments, the X-ray powder diffraction pattern further comprising at least one peak selected from 5.44±0.2° 2-θ, 20.78±0.2° 2-θ, 22.74±0.2° 2-θ, 23.04±0.2° 2-θ, 26.80±0.2° 2-θ, and 28.86±0.2° 2-θ, and as measured by X-ray powder diffraction using an X-ray wavelength of 0.71073 Å. In some embodiments, the X-ray powder diffraction pattern further comprising at least five peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the crystalline composition is characterized by an X-ray powder diffraction pattern substantially the same as shown in FIG. 1.

In some embodiments, the crystalline composition is characterized by a differential scanning calorimetry (DSC) thermogram comprising an endotherm in the range of about 160° C. to 170° C. In some embodiments, the crystalline composition is characterized by a differential scanning calorimetry (DSC) thermogram comprising an endotherm with an onset of about 164° C. and a peak of about 166° C. In some embodiments, the crystalline composition is characterized by a melting point of about 166° C. In some embodiments, the crystalline composition is characterized by a differential scanning calorimetry (DSC) thermogram substantially the same as shown in FIG. 2.

In some embodiments, the crystalline composition is characterized by a thermogravimetric analysis (TGA) thermogram comprising a loss in mass of about 11% over a temperature range of about 25° C. to about 200° C. In some embodiments, the crystalline composition is characterized by a thermogravimetric analysis (TGA) thermogram substantially the same as shown in FIG. 3.

In some embodiments, the crystalline composition is characterized by a dynamic vapor sorption (DVS) trace substantially the same as shown in FIG. 4.

In a second aspect, the present disclosure provides a pharmaceutical composition comprising crystalline composition according to Formula I:

Formula I

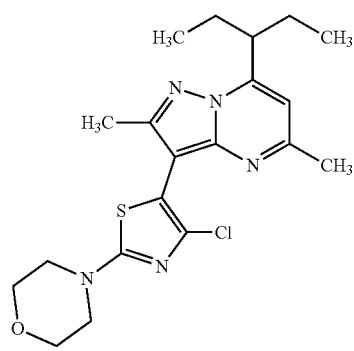 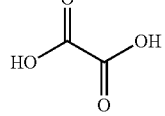 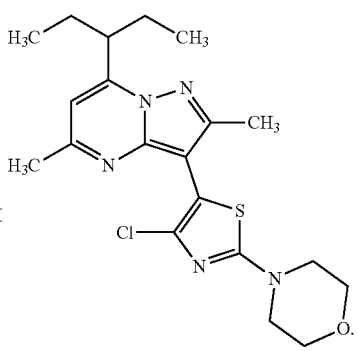

and at least one pharmaceutically acceptable carrier or excipient.

In a third aspect, the present disclosure provides a method of preparing a crystalline composition according to Formula I:

Formula I

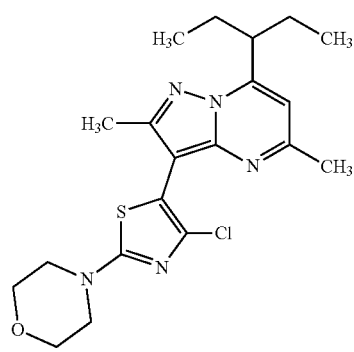 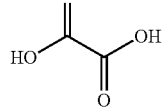 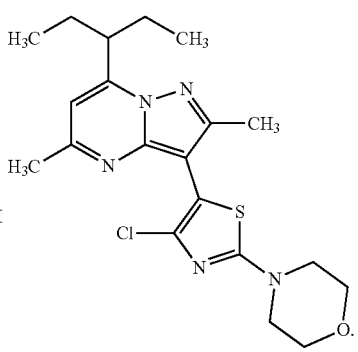

wherein the method comprises:
a) dissolving 4-(4-chloro-5-(2,5-dimethyl-7-(pentan-3-yl)pyrazolo[1,5-a]pyrimidin-3-yl)thiazol-2-yl)morpholine (Compound 1) and oxalic acid in a solvent;
b) heating the solution or slurry from step (a); and
c) crystallizing the solution or slurry obtained in step (b) to obtain the crystalline composition according to Formula I.

In some embodiments of the method of preparing the crystalline composition according to Formula I, the solvent in step (a) comprises acetone, heptane, water, 2-butanol, ethyl acetate, 2-propanol, methyl tert-butyl ether, ethanol, methyl ethyl ketone, 1-pentanol, or a combination thereof. In some embodiments, the solvent in step (a) is heptane. In some embodiments, the solvent in step (a) is methyl tert-butyl ether or methyl ethyl ketone. In some embodiments, the solvent in step (a) is a mixture of heptane and methyl ethyl ketone. In some embodiments, step (b) is heated at about 50° C.

In another aspect, the present disclosure provides a method of treating or preventing testicular adrenal rest tumors (TART) or ovarian adrenal rest tumors (OART) in a subject in need thereof, comprising administering to the subject a crystalline composition according to Formula I as described herein, or the pharmaceutical composition comprising the crystalline composition according to Formula I as described herein. In some embodiments, the subject has congenital adrenal hyperplasia (CAH).

In another aspect, the present disclosure provides a method of treating congenital adrenal hyperplasia (CAH) in a subject in need thereof, comprising administering to the subject a crystalline composition according to Formula I as described herein, or a pharmaceutical composition comprising the crystalline composition according to Formula I as described herein. In some embodiments, the CAH is a classic CAH. In some embodiments, the CAH is a non-classical CAH.

In another aspect, the present disclosure provides a method of improving hyperandrogenic symptoms in a subject in need thereof, comprising administering to the subject a crystalline composition according to Formula I as described herein, or the pharmaceutical composition comprising the crystalline composition according to Formula I as described herein. In some embodiments, the hyperandrogenic symptoms are selected from the group consisting of acne, hirsutism, and alopecia.

In another aspect, the present disclosure provides a method of treating menstrual irregularity, ovulatory dysfunction or infertility, in a subject in need thereof, comprising administering to the subject a crystalline composition according to Formula I as described herein, or the pharmaceutical composition comprising the crystalline composition according to Formula I as described herein.

In another aspect, the present disclosure provides a method of improving metabolic symptoms in a subject in need thereof, comprising administering to the subject a crystalline composition according to Formula I as described herein, or the pharmaceutical composition comprising the crystalline composition according to Formula I as described herein. In some embodiments, the metabolic symptoms are selected from the group consisting of body weight, BMI, fat mass, waist circumference, blood pressure and glycemic control.

In another aspect, the present disclosure provides a method of treating polycystic ovary syndrome with functional ovarian hyperandrogenism and functional adrenal hyperandrogenism (PCOS-FOH+FAH) in a subject in need thereof, comprising administering to the subject a crystalline composition according to Formula I as described herein, or the pharmaceutical composition comprising the crystalline composition according to Formula I as described herein.

In another aspect, the present disclosure provides a method of treating polycystic ovary syndrome with functional adrenal hyperandrogenism (PCOS-FAH) in a subject in need thereof, comprising administering to the subject a crystalline composition according to Formula I as described herein, or the pharmaceutical composition comprising the crystalline composition according to Formula I as described herein.

In another aspect, the present disclosure provides a method of treating endometriosis or improving the symptoms of endometriosis in a subject in need thereof, comprising administering to the subject a crystalline composition according to Formula I as described herein, or the pharmaceutical composition comprising the crystalline composition according to Formula I as described herein. In some embodiments, the administration of the crystalline composition or the pharmaceutical composition improves the symptom of pain experienced by the subject. In some embodiments, the administration of the crystalline composition or the pharmaceutical composition reduces the symptoms of pain experienced by the subject. In some embodiments, the administration of the crystalline composition or the pharmaceutical composition prevents the symptom of pain experienced by the subject. In some embodiments, the administration of the crystalline composition or the pharmaceutical composition eliminates the symptom of pain experienced by the subject.

In various embodiments of the methods as described herein, the crystalline composition or the pharmaceutical composition is administered at a dose from about 5 mg/day to about 1000 mg/day. In some embodiments, the crystalline composition or the pharmaceutical composition is administered in a fed state. In some embodiments, the crystalline composition or the pharmaceutical composition is administered in a fasted state. In some embodiments, the crystalline composition or the pharmaceutical composition is administered at least once per day.

In various embodiments of the methods as described herein, the method further comprises administering to the subject an additional chemotherapeutic agent. In some embodiments, the additional chemotherapeutic agent is glucocorticoid, a mineralocorticoid, an ACAT1 inhibitor, or an anti-androgen agent. In some embodiments, the glucocorticoid is beclomethasone, betamethasone, budesonide, cortisone, dexamethasone, hydrocortisone, methylprednisolone, prednisolone, prednisone, or triamcinolone. In some embodiments, the mineralocorticoid is fludrocortisone. In some embodiments, the additional chemotherapeutic agent is another CRF1 antagonist.

In various embodiments of the methods as described herein, the method further comprises an additional treatment selected from surgical resection of the tumors and radiation therapy, or a combination thereof. In some embodiments, the additional therapy is surgical resection and the surgical resection is prior to, after, and/or concurrent with administration of the crystalline composition as described herein, or the pharmaceutical composition comprising the crystalline composition as described herein. In some embodiments, the additional therapy is radiation therapy and the radiation therapy is prior to, after, and/or concurrent with administration of the crystalline composition as described herein, or the pharmaceutical composition comprising the crystalline composition as described herein.

In various embodiments of the methods, the subject is from about 9 years of age to about 18 years of age. In some embodiments, the subject is from about 8 years of age to about 55 years of age.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DESCRIPTION OF THE DRAWINGS

The novel features of the present disclosure are set forth with particularity in the appended claims. An understanding of the features and advantages of the present disclosure may be obtained by reference to the following detailed description that sets forth illustrative embodiments, in which the principles of the present disclosure are utilized, and the accompanying drawings of which:

Figure 1:
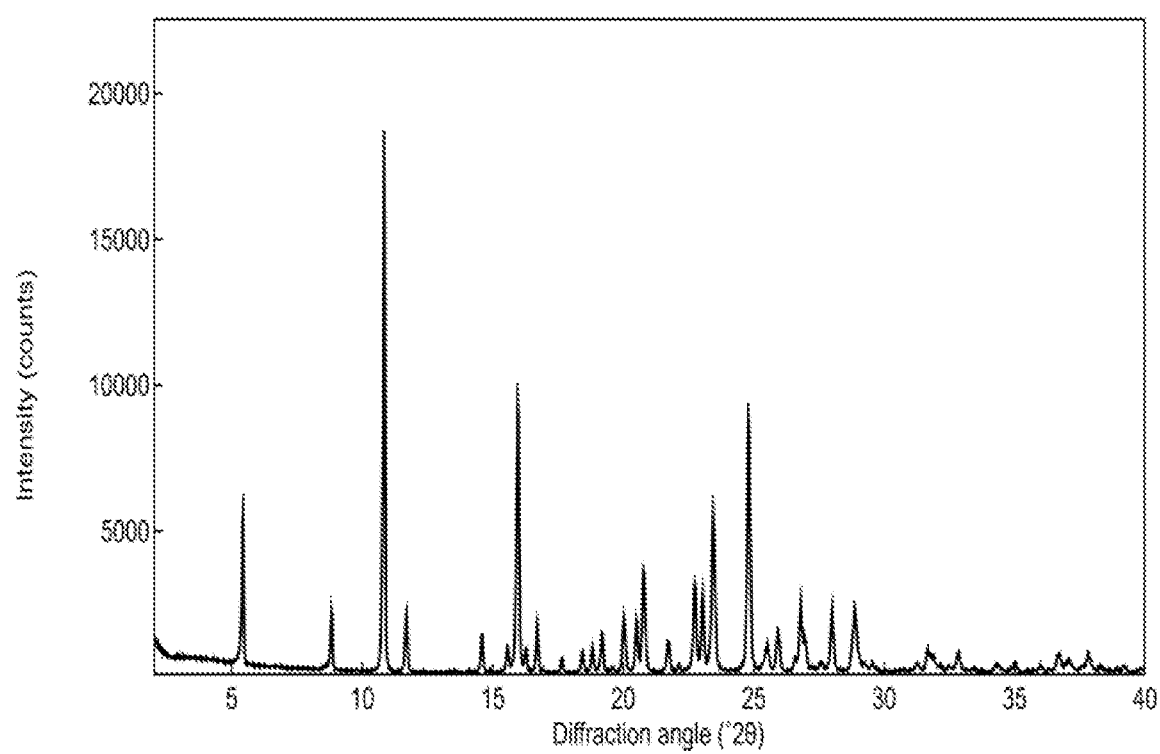
FIG. 1 shows the X-ray powder diffraction (XRPD) pattern for the crystalline composition according to Formula I.

DETAILED DESCRIPTION OF THE INVENTION 4-(4-chloro-5-(2,5-dimethyl-7-(pentan-3-yl)pyrazolo[1,5-a]pyrimidin-3-yl)thiazol-2-yl)morpholine (Compound 1) is a potent antagonist of Corticotropin-releasing hormone receptor 1 (CRF1). CRF1 antagonists are useful in the treatment of various diseases, conditions, and disorders for which abnormal CRF1 activity plays a role.

Crystalline forms of a small molecule drug candidate, such as a CRF1 antagonist, can have different physical properties, including melting point, apparent solubility, dissolution rate, optical and mechanical properties, vapor pressure, and density. These properties can have a direct effect on the ability to process or manufacture a drug substance and the drug product. Moreover, differences in these properties can and often lead to different pharmacokinetics profiles for different polymorphic forms of a drug. Polymorphism can affect the quality, safety, and/or efficacy of a drug product, such as a CRF1 antagonist. Thus, there still remains a need for crystalline compositions of CRF1 antagonist. The present disclosure addresses this need and provides related advantages as well.

Compound 1

As described herein, Compound 1 refers to 4-(4-chloro-5-(2,5-dimethyl-7-(pentan-3-yl)pyrazolo[1,5-a]pyrimidin-3-yl)thiazol-2-yl)morpholine, which has the chemical structure as shown below:

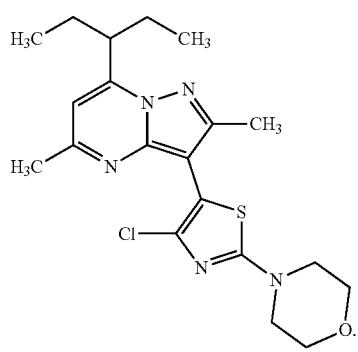

Compound 1

Compound 1 is a CRF1 modulator. CRF1 modulator, such as a CRF1 antagonist or inhibitor, are useful in the treatment of various conditions and disorders that are mediated by CRF1 activities.

In some embodiments, the present disclosure provides a crystalline composition comprising compound 1. In some embodiments, the crystalline composition comprises Compound 1 and oxalic acid in a molar ratio of 2:1.

As used herein, "crystalline," "crystalline form," "polymorph," "Form," and "form" may be used interchangeably herein, and are meant to include all crystalline and amorphous forms of the compound, including, for example, co-crystals, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to. Compounds of the present disclosure include crystalline and amorphous forms of those compounds, including, for example, polymorphs, co-crystals, pseudopolymorphs, solvates, hydrates, unsolvated polymorphs (including anhydrates), conformational polymorphs, and amorphous forms of the compounds, as well as mixtures thereof.

As used herein, "co-crystal" may be used to describe crystalline compositions comprising multi-component crystals based on hydrogen bonding interactions of hydrogen ions to form salt forms. In some embodiments, the crystalline composition as described herein are co-crystals comprising oxalic acid and Compound 1.

Definitions

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, such as those known in the art, for example, described in Remington's Pharmaceutical Sciences 16th edition, Osol, A. Ed. (1980).

As used herein, "treatment" or "treating" is an approach for obtaining beneficial or desired results including and preferably clinical results. For example, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. The protein may be deoxycytidine kinase. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets.

"Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a compound described herein is administered at the same time, just prior to, or just after the administration of one or more additional therapies, for example, an anticancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. In some embodiments, the active and/or adjunctive agents are linked or conjugated to one another. In some embodiments, the compounds described herein are combined with treatments for cancer such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. A "cancer-patient" is a patient suffering from, or prone to developing cancer.

Unless clearly indicated otherwise, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. In some embodiments, the invention find use in both human medicine and in the veterinary context.

"Disease" or "condition" refer to a state of being or health status of a patient or subject capable of being treated with the compounds or methods provided herein. In some embodiments, the disease as used herein refers to cancer.

As used herein and in the appended claims, the singular forms "a," "an," and "the" include plural reference unless the context clearly indicates otherwise.

It is understood that aspect and variations of the invention described herein include "consisting" and/or "consisting essentially of" aspects and variations.

Crystalline Composition According to Formula I

The crystalline composition prepared according to the methods of the present disclosure may be characterized by any methodology according to the art. For example, the crystalline composition according to Formula I prepared according to the methods of the present disclosure may be characterized by X-ray powder diffraction (XRPD), differential scanning calorimetry (DSC), thermogravimetric analysis (TGA), and/or spectroscopy (e.g., Raman, solid state nuclear magnetic resonance (ssNMR), proton nuclear magnetic resonance ($^1$H NMR), and infrared (IR)). In some embodiments, crystallinity of the solid form is determined by X-Ray Powder Diffraction (XPRD).

XRPD: Crystalline composition according to the present disclosure may be characterized by XRPD. The relative intensities of XRPD peaks can vary, depending upon the particle size, the sample preparation technique, the sample mounting procedure and the particular instrument employed. Moreover, instrument variation and other factors can affect the 2-θ values. Therefore, the XRPD peak assignments can vary, for example by plus or minus about 0.2 degrees.

Figure 2:
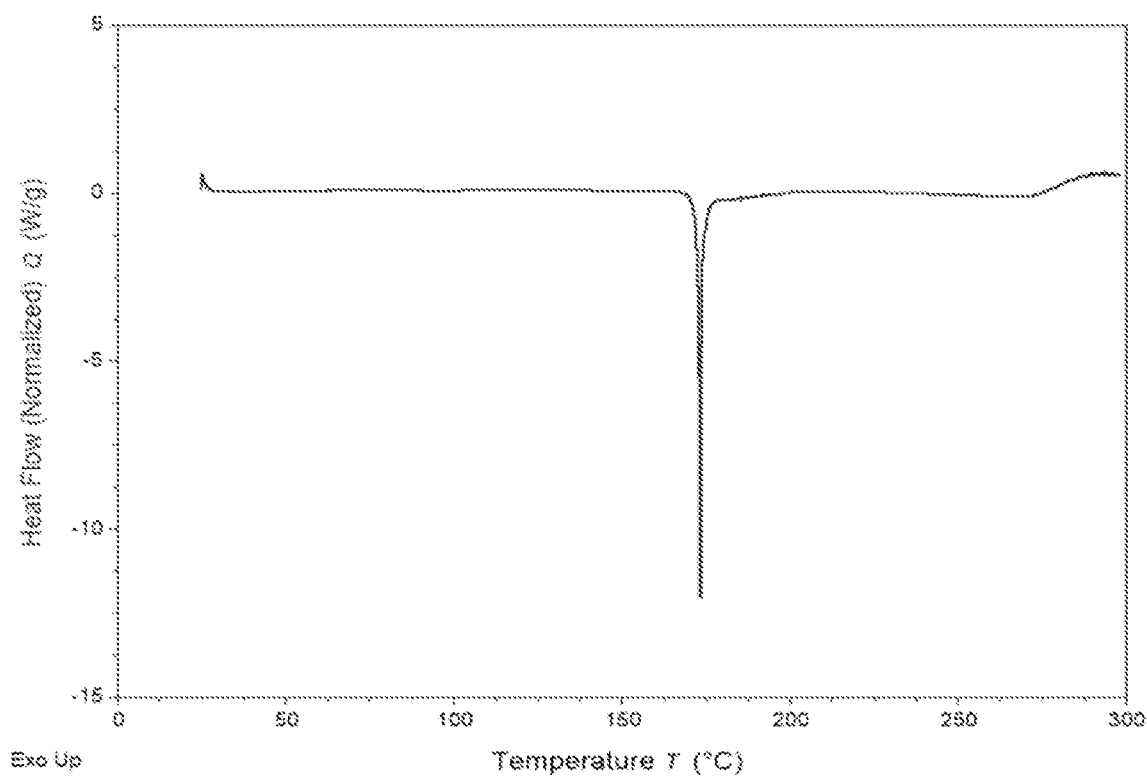
FIG. 2 shows the differential scanning calorimetry (DSC) thermogram for the crystalline composition according to Formula I.

DSC: Crystalline composition according to the present disclosure can also be identified by its characteristic DSC thermograms such as shown in FIG. 2. For DSC, it is known that the temperatures observed will depend upon the rate of temperature change as well as sample preparation technique and the particular instrument employed. Thus, the values reported herein relating to DSC thermograms can vary, for example by plus or minus about 4° C.

TGA: Crystalline composition according to the present disclosure may also give rise to thermal behavior different from that of the amorphous material or other crystalline forms. Thermal behavior may be measured in the laboratory by thermogravimetric analysis (TGA) which may be used to distinguish some crystalline forms from others. In one aspect, the crystalline composition as described herein may be characterized by thermogravimetric analysis.

DVS: Crystalline composition according to the present disclosure may also give rise to vapors sorption behavior different from that of the amorphous material or other crystalline forms. The vapor sorption behavior may be measured in the laboratory by dynamic vapor sorption (DVS) which may be used to distinguish some crystalline forms from others. In one aspect, the crystalline composition as described herein may be characterized by dynamic vapor sorption.

The crystalline composition comprising Compound 1, e.g. according to Formula I, are useful in the production of medicinal preparations and can be obtained by means of a crystallization process to produce crystalline and semi-crystalline forms or a solidification process to obtain the amorphous form. In various embodiments, the crystallization is carried out by either generating the desired compound (for example Compound 1) in a reaction mixture and isolating the desired crystalline composition from the reaction mixture, or by dissolving raw compound in a solvent, optionally with heat, followed by crystallizing/solidifying the product by cooling (including active cooling) and/or by the addition of an antisolvent for a period of time. The crystallization or solidification may be followed by drying carried out under controlled conditions until the desired water content is reached in the end crystalline composition.

FIG. 1 shows the X-ray powder diffraction (XRPD) pattern for the crystalline composition according to Formula I.

FIG. 2 shows the differential scanning calorimetry (DSC) thermogram for the crystalline composition according to Formula I.

Figure 3:
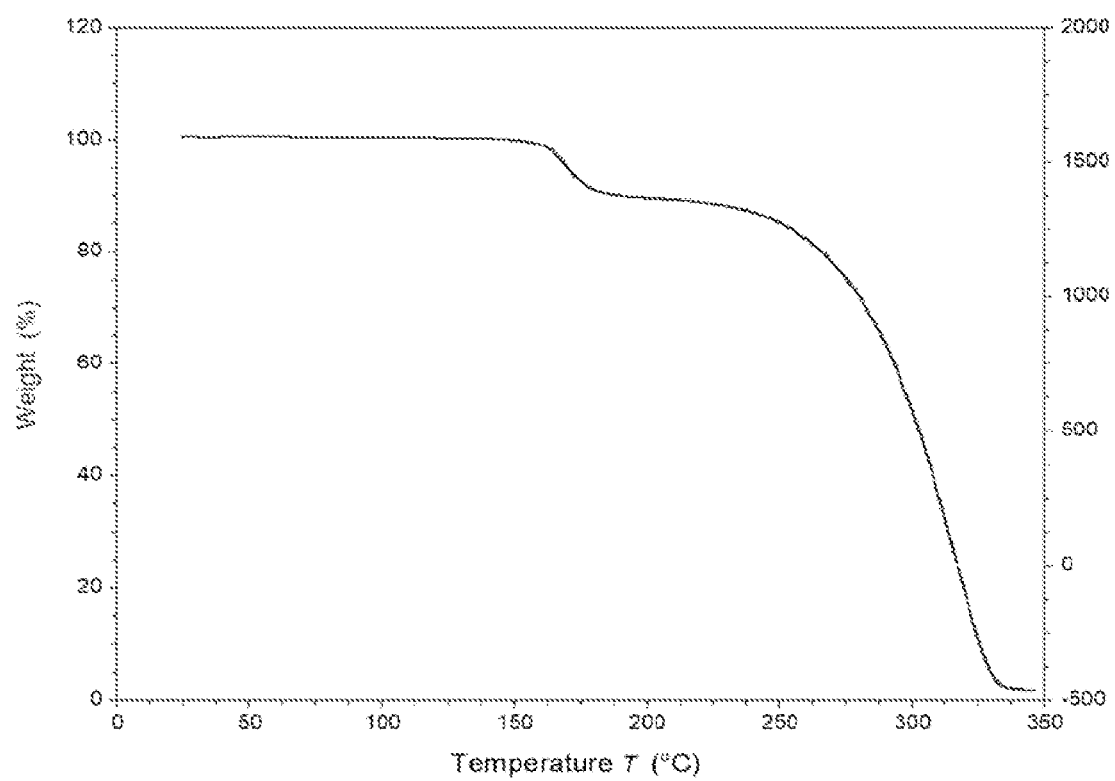
FIG. 3 shows the thermogravimetric analysis (TGA) thermogram for the crystalline composition according to Formula I.

FIG. 3 shows the thermogravimetric analysis (TGA) thermogram for the crystalline composition according to Formula I.

Figure 4:
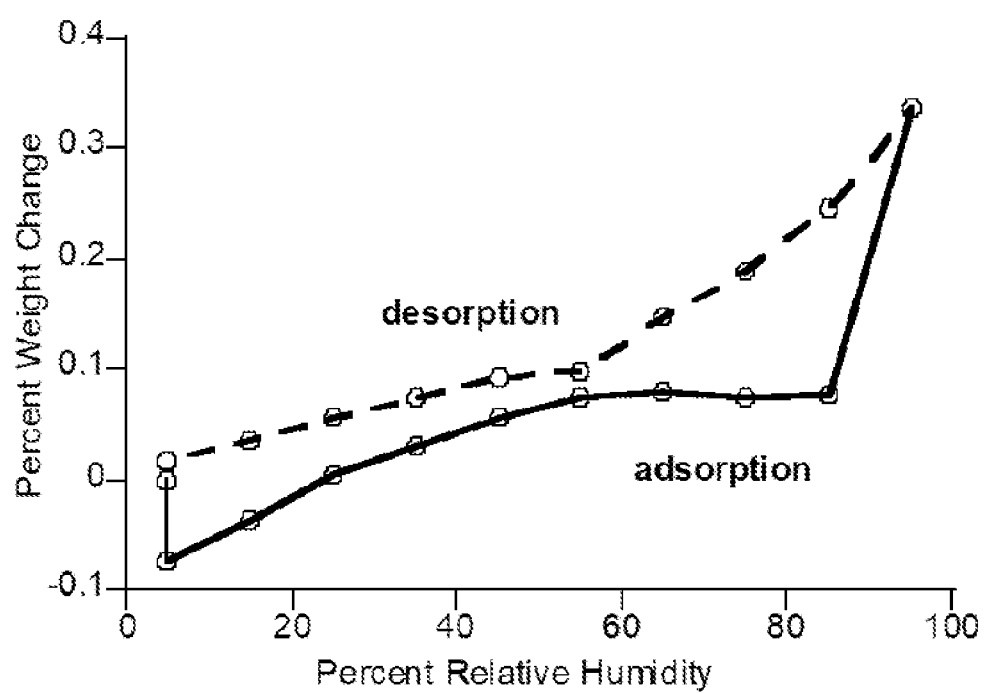
FIG. 4 shows the dynamic vapor sorption (DVS) trace for the crystalline composition according to Formula I.

FIG. 4 shows the dynamic vapor sorption (DVS) trace for the crystalline composition according to Formula I.

Figure 5:
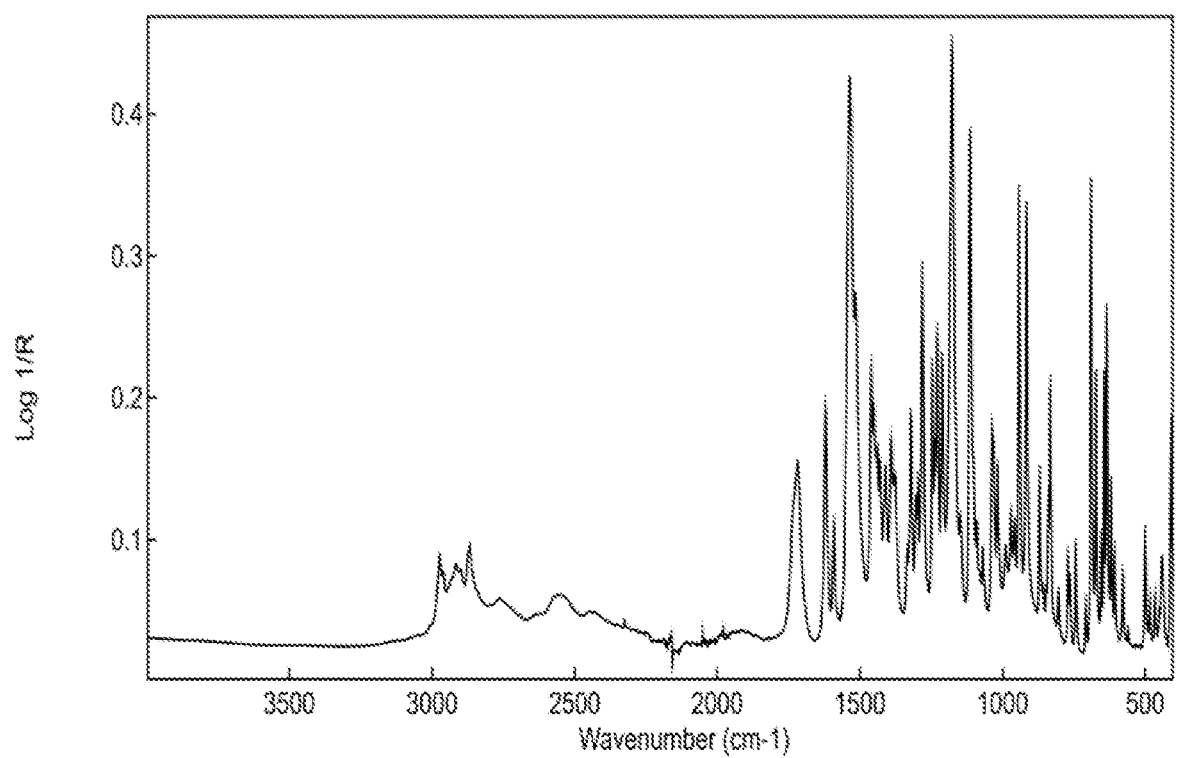
FIG. 5 shows the infrared (IR) spectrum for the crystalline composition according to Formula I.

FIG. 5 shows the infrared (IR) spectrum for the crystalline composition according to Formula I.

Figure 6:
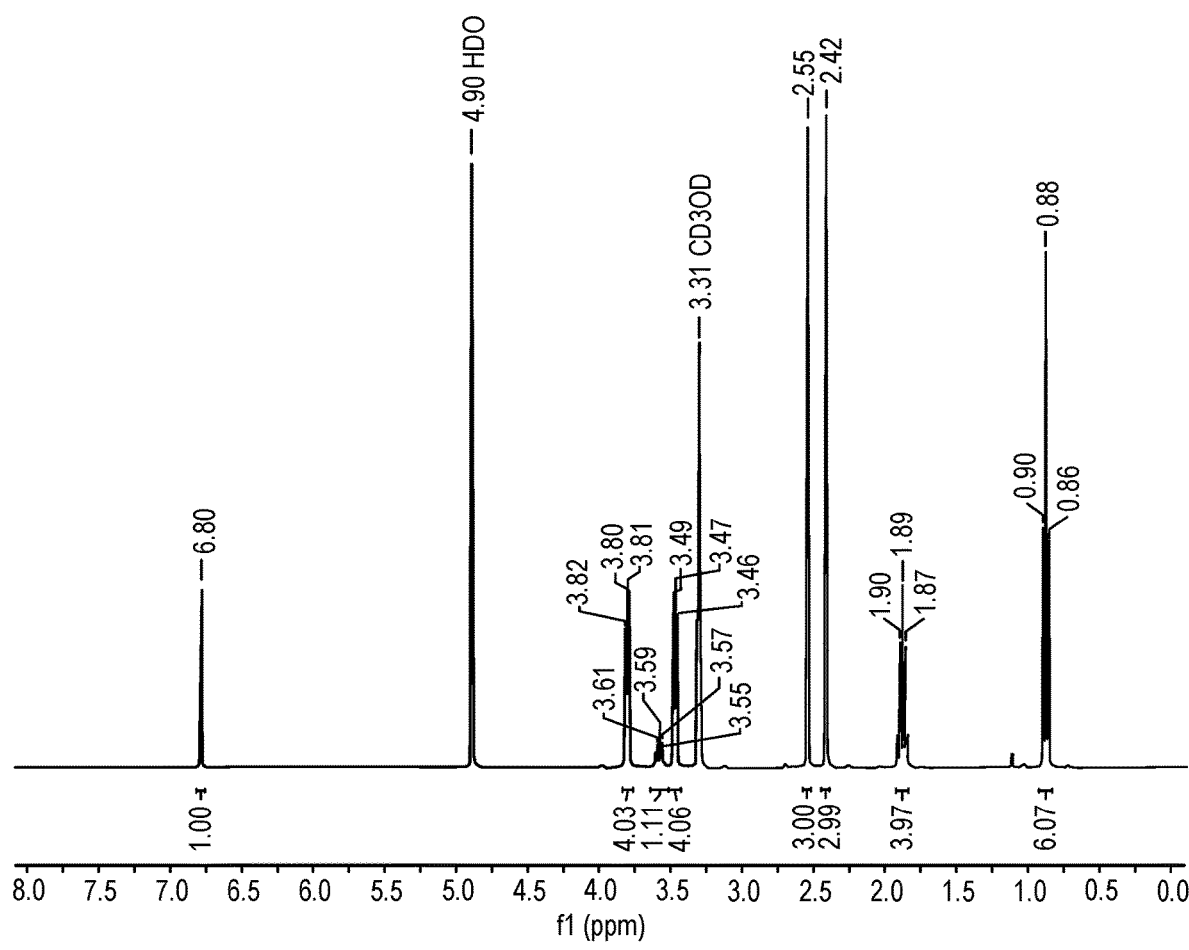
FIG. 6 shows the proton nuclear magnetic resonance ($^1$H NMR) spectrum for the crystalline composition according to Formula I.

FIG. 6 shows the proton nuclear magnetic resonance ($^1$H NMR) spectrum for the crystalline composition according to Formula I.

Figure 7:
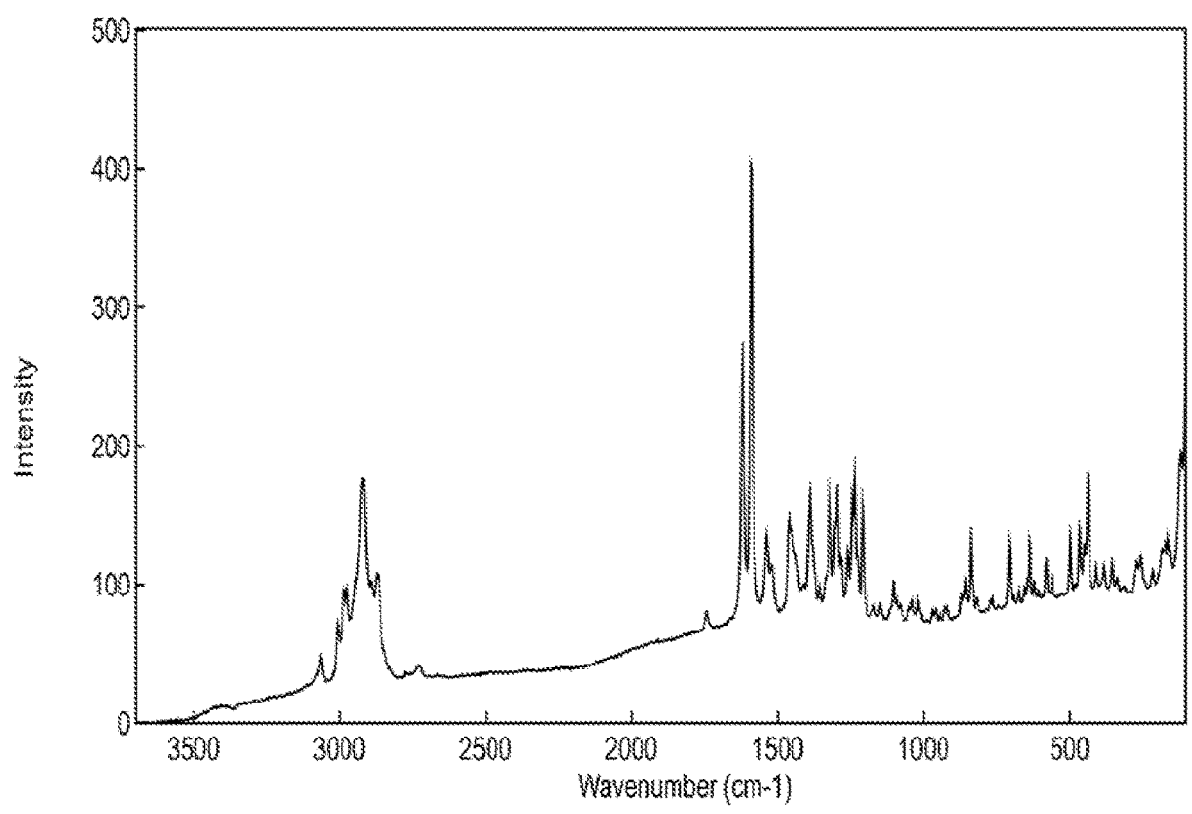
FIG. 7 shows the Raman spectrum for the crystalline composition according to Formula I.

FIG. 7 shows the Raman spectrum for the crystalline composition according to Formula I.

In a first aspect, the present disclosure provides a crystalline composition according Formula I:

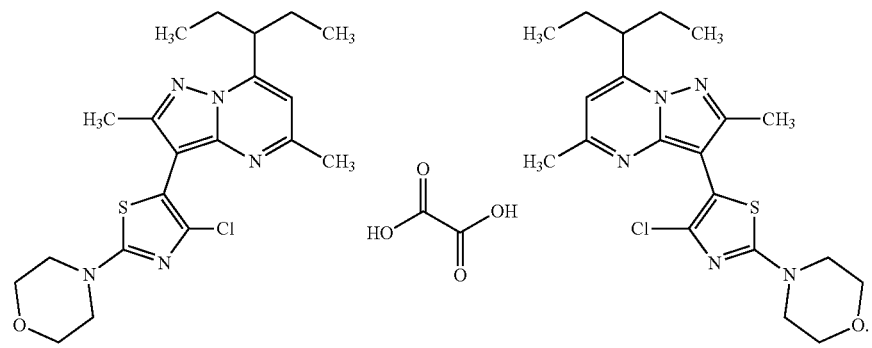

Formula I

In some embodiments, the crystals of the crystalline composition according to Formula I have unit cell parameters at T=150° K of: a=34.003(4) Å, b=6.5843(13) Å, c=21.062(5) Å; β=108.703(12)°, V=4466.5(15) Å$^3$ and a monoclinic C2/c space group.

In some embodiments, the crystals of the crystalline composition according to Formula I is characterized by:
(a) an X-ray powder diffraction pattern comprising peaks at 10.84±0.2° 2-θ, 15.96±0.2° 2-θ, 23.44±0.2° 2-θ, and 24.80±0.2° 2-θ, and as measured by X-ray powder diffraction using an X-ray wavelength of 0.71073 Å;
(b) an X-ray powder diffraction pattern substantially the same as shown in FIG. 1;
(c) a differential scanning calorimetry (DSC) thermogram comprising an endotherm in the range of about 160° C. to 170° C.;
(d) a differential scanning calorimetry (DSC) thermogram comprising an endotherm with an onset of about 164° C. and a peak of about 166° C.;
(e) a differential scanning calorimetry (DSC) thermogram substantially the same as shown in FIG. 2;
(f) a thermogravimetric analysis (TGA) thermogram comprising a loss in mass of about 11% over a temperature range of about 25° C. to about 200° C.;
(g) a thermogravimetric analysis (TGA) thermogram substantially the same as shown in FIG. 3; or
(h) combinations thereof.

In some embodiments, the crystalline composition according to Formula I is characterized by an X-ray powder diffraction pattern comprising peaks at 10.84±0.2° 2-θ, 15.96±0.2° 2-θ, 23.44±0.2° 2-θ, and 24.80±0.2° 2-θ, and as measured by X-ray powder diffraction using an X-ray wavelength of 0.71073 Å. In some embodiments, the crystalline composition according to Formula I is characterized by an X-ray powder diffraction pattern comprising peaks at 10.84±0.1° 2-θ, 15.96±0.1° 2-θ, 23.44±0.1° 2-θ, and 24.80±0.1° 2-θ, and as measured by X-ray powder diffraction using an X-ray wavelength of 0.71073 Å. In some embodiments, the crystalline composition according to Formula I is characterized by an X-ray powder diffraction pattern comprising peaks at about 10.84° 2-θ, about 15.96° 2-θ, about 23.44° 2-θ, and about 24.80° 2-θ, and as measured by X-ray powder diffraction using an X-ray wavelength of 0.71073 Å.

In some embodiments, the X-ray powder diffraction pattern further comprising at least one peak selected from 5.44±0.2° 2-θ, 20.78±0.2° 2-θ, 22.74±0.2° 2-θ, 23.04±0.2° 2-θ, 26.80±0.2° 2-θ, and 28.86±0.2° 2-θ, and as measured by X-ray powder diffraction using an X-ray wavelength of 0.71073 Å. In some embodiments, the X-ray powder diffraction pattern further comprising at least one peak selected from 5.44±0.1° 2-θ, 20.78±0.1° 2-θ, 22.74±0.1° 2-θ, 23.04±0.1° 2-θ, 26.80±0.1° 2-θ, and 28.86±0.1° 2-θ, and as measured by X-ray powder diffraction using an X-ray wavelength of 0.71073 Å. In some embodiments, the X-ray powder diffraction pattern further comprising at least one peak selected from about 5.44° 2-θ, about 20.78° 2-θ, about 22.74° 2-θ, about 23.04° 2-θ, about 26.80° 2-θ, and about 28.86° 2-θ, and as measured by X-ray powder diffraction using an X-ray wavelength of 0.71073 Å.

In some embodiments, the X-ray powder diffraction pattern further comprising at least one peak selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least two peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least three peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least four peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least five peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least six peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least seven peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern further comprising at least eight peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å. In some embodiments, the X-ray powder diffraction pattern comprises peaks selected from 8.82±0.1° 2-θ, 11.70±0.1° 2-θ, 14.60±0.1° 2-θ, 15.56±0.1° 2-θ, 16.70±0.1° 2-θ, 18.82±0.1° 2-θ, 19.18±0.1° 2-θ, 20.02±0.1° 2-θ, 20.50±0.1° 2-θ, 21.72±0.1° 2-θ, 25.52±0.1° 2-θ, 25.92±0.1° 2-θ, 26.94±0.1° 2-θ, and 28.00±0.1° 2-θ, and as measured by X-ray powder diffraction using an X-ray wavelength of 0.71073 Å. In some embodiments, the X-ray powder diffraction pattern comprises peaks selected from 8.82° 2-θ, 11.70° 2-θ, 14.60° 2-θ, 15.56° 2-θ, 16.70° 2-θ, 18.82° 2-θ, 19.18° 2-θ, 20.02° 2-θ, 20.50° 2-θ, 21.72° 2-θ, 25.52° 2-θ, 25.92° 2-θ, 26.94° 2-θ, and 28.00° 2-θ, and as measured by X-ray powder diffraction using an X-ray wavelength of 0.71073 Å.

In some embodiments, the crystalline composition according to Formula I is characterized by a differential scanning calorimetry (DSC) thermogram comprising an endotherm in the range of about 160° C. to 170° C. In some embodiments, the crystalline composition is characterized by a differential scanning calorimetry (DSC) thermogram comprising an endotherm with an onset of about 164° C. and a peak of about 166° C. In some embodiments, the crystalline composition is characterized by a melting point of about 166° C. In some embodiments, the crystalline composition is characterized by a differential scanning calorimetry (DSC) thermogram substantially the same as shown in FIG. 2.

In some embodiments, the crystalline composition according to Formula I is characterized by a differential scanning calorimetry (DSC) thermogram comprising an endotherm at about 160° C. to about 170° C., about 160° C. to about 169° C., about 160° C. to about 168° C., about 160° C. to about 167° C., about 160° C. to about 166° C., about 160° C. to about 165° C., about 160° C. to about 164° C., about 160° C. to about 163° C., about 160° C. to about 162° C., about 160° C. to about 161° C., about 161° C. to about 170° C., about 162° C. to about 170° C., about 163° C. to about 170° C., about 164° C. to about 170° C., about 165° C. to about 170° C., about 166° C. to about 170° C., about 167° C. to about 170° C., about 168° C. to about 170° C., or about 169° C. to about 170° C. In some embodiments, the crystalline composition according to Formula I is characterized by a differential scanning calorimetry (DSC) thermogram comprising an endotherm at about 162° C. to about 166° C., for example at about 162° C., about 163° C., about 164° C., 165° C., or 166° C. In some embodiments, the crystalline composition is characterized by a differential scanning calorimetry (DSC) thermogram comprising an endotherm at about 164° C. In some embodiments, the crystalline composition according for Formula I has a melting point of about 166° C.

In some embodiments, the crystalline composition according to Formula I is characterized by a thermogravimetric analysis (TGA) thermogram comprising a loss in mass of about 11% over a temperature range of about 25° C. to about 200° C. In some embodiments, the crystalline composition decomposes above a temperature of about 50° C., about 100° C., about 150° C., about 200° C., about 250° C., about 300° C., about 350° C., or about 400° C. In some embodiments, the crystalline composition decomposes above a temperature of about 200° C. In some embodiments, the crystalline composition decomposes above a temperature of about 250° C. In some embodiments, the crystalline composition is characterized by a thermogravimetric analysis (TGA) thermogram substantially the same as shown in FIG. 3.

In some embodiments, the crystalline composition according to Formula I is characterized by a dynamic vapor sorption (DVS) trace substantially the same as shown in FIG. 4.

In some embodiments, the crystalline composition according to Formula I is anhydrous.

In some embodiments, the crystalline composition according to Formula I is stable at room temperature. In some examples, the crystalline composition according to Formula I can be stored at room temperature for an extended period of time without significant chemical degradation or change in the crystalline form. In some examples, crystalline composition according to Formula I can be stored at room temperature for a timer period of at least about 10 days, 30 days, 60 days, 90 days, 120 days, 150 days, or 180 days. In some examples, the crystalline composition can be stored at room temperature for a time period of more than about 180 days. In some examples, the crystalline composition can be stored at room temperature for a time period of 10-14 days, 10-18 days, 10-22 days, 10-26 days, 10-30 days, 10-40 days, 10-50 days, 10-60 days, 10-90 days, 10-120 days, 10-150 days, 10-180 days, 14-18 days, 14-22 days, 14-26 days, 14-30 days, 14-40 days, 14-50 days, 14-60 days, 14-90 days, 14-120 days, 14-150 days, 14-180 days, 18-22 days, 18-26 days, 18-30 days, 18-40 days, 18-50 days, 18-60 days, 18-90 days, 18-120 days, 18-150 days, 18-180 days, 22-26 days, 22-30 days, 22-40 days, 22-50 days, 22-60 days, 22-90 days, 22-120 days, 22-150 days, 22-180 days, 26-30 days, 26-40 days, 26-50 days, 26-60 days, 26-90 days, 26-120 days, 26-150 days, 26-180 days, 30-40 days, 30-50 days, 30-60 days, 30-90 days, 30-120 days, 30-150 days, 30-180 days, 40-50 days, 40-60 days, 40-90 days, 40-120 days, 40-150 days, 40-180 days, 50-60 days, 50-90 days, 50-120 days, 50-150 days, 50-180 days, 60-90 days, 60-120 days, 60-150 days, 60-180 days, 90-120 days, 90-150 days, or 90-180 days. In some examples, the crystalline composition can be stored at room temperature for a time period of at least 10 days, 14 days, 18 days, 22 days, 26 days, 30 days, 40 days, 50 days, 60 days, 90 days, 120 days, 150 days, or 180 days.

In some embodiments, the crystalline composition according to Formula I is stable at room temperature or temperatures above the room temperature and/or at high relative humidity (RH). In some examples, the crystalline composition can be stored at about 25° C. and at about 75% RH for an extended period of time without significant chemical degradation or change in the crystalline form. In some examples, the crystalline composition according to Formula I can be stored at about 25° C. and at about 75% RH for a time period of at least about 10 days, 30 days, 60 days, 90 days, 120 days, 150 days, or 180 days. In some examples, the crystalline composition can be stored at about 25° C. and at about 75% RH for a time period of 10-14 days, 10-18 days, 10-22 days, 10-26 days, 10-30 days, 10-40 days, 10-50 days, 10-60 days, 10-90 days, 10-120 days, 10-150 days, 10-180 days, 14-18 days, 14-22 days, 14-26 days, 14-30 days, 14-40 days, 14-50 days, 14-60 days, 14-90 days, 14-120 days, 14-150 days, 14-180 days, 18-22 days, 18-26 days, 18-30 days, 18-40 days, 18-50 days, 18-60 days, 18-90 days, 18-120 days, 18-150 days, 18-180 days, 22-26 days, 22-30 days, 22-40 days, 22-50 days, 22-60 days, 22-90 days, 22-120 days, 22-150 days, 22-180 days, 26-30 days, 26-40 days, 26-50 days, 26-60 days, 26-90 days, 26-120 days, 26-150 days, 26-180 days, 30-40 days, 30-50 days, 30-60 days, 30-90 days, 30-120 days, 30-150 days, 30-180 days, 40-50 days, 40-60 days, 40-90 days, 40-120 days, 40-150 days, 40-180 days, 50-60 days, 50-90 days, 50-120 days, 50-150 days, 50-180 days, 60-90 days, 60-120 days, 60-150 days, 60-180 days, 90-120 days, 90-150 days, or 90-180 days. In some examples, the crystalline composition according to Formula I can be stored at about 25° C. for a time period of at least 10 days, 14 days, 18 days, 22 days, 26 days, 30 days, 40 days, 50 days, 60 days, 90 days, 120 days, 150 days, or 180 days.

In some embodiments, the crystalline composition according to Formula I is thermodynamically stable.

In some embodiments, the crystalline composition according to Formula I is highly bioavailable.

In some embodiments, the crystalline composition according to Formula I is stable under accelerated storage conditions.

In some embodiments, the crystalline composition according to Formula I is characterized by an infrared (IR) spectrum substantially the same as shown in FIG. 5.

In some embodiments, the crystalline composition according to Formula I is characterized by a proton nuclear magnetic resonance ($^1$H NMR) spectrum substantially the same as shown in FIG. 6.

In some embodiments, the crystalline composition according to Formula I is characterized by a Raman spectrum substantially the same as shown in FIG. 7.

Compositions and Formulations

In a second aspect, the present disclosure provides a pharmaceutical composition comprising a crystalline composition according to Formula I:

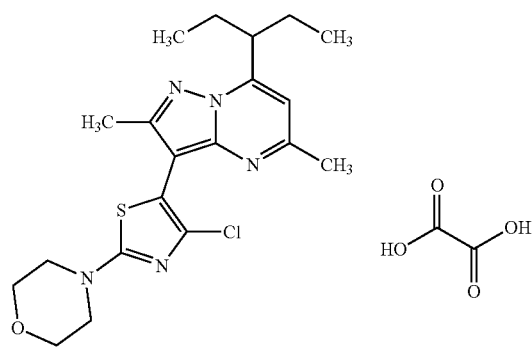 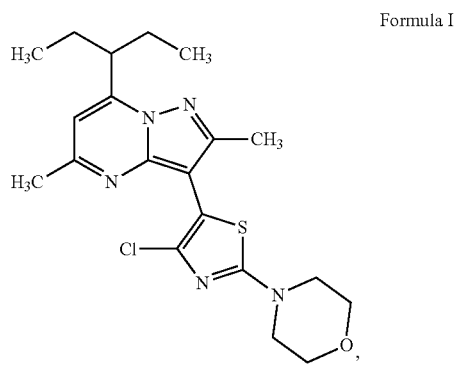

Formula I and at least one pharmaceutically acceptable carrier or excipient.

Dosage Form

In some embodiments, the pharmaceutical composition described herein is provided in unit dosage form. As used herein, a "unit dosage form" is a composition containing an amount of the crystalline composition according to Formula I that is suitable for administration to a subject in a single dose. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded.

In some embodiments, the pharmaceutical compositions described herein are formulated as oral dosage forms. Suitable oral dosage forms include, for example, tablets, pills, sachets, or capsules. In some embodiments, the pharmaceutical composition comprises one or more additional pharmaceutically acceptable excipients. See, e.g., Remington: The Science and Practice of Pharmacy (Gennaro, 21st Ed. Mack Pub. Co., Easton, Pa. (2005) for a list of pharmaceutically acceptable excipients.

Capsule

In some embodiments, the pharmaceutical composition comprising the crystalline composition according to Formula I is formulated as a capsule. In some embodiments, the pharmaceutical composition is encapsulated in a hard gel capsule. In some embodiments, the pharmaceutical composition is encapsulated in a soft gel capsule. In some embodiments, the pharmaceutical composition is formulated as a hard gel capsule. In some embodiments, the pharmaceutical composition is formulated as a soft gel capsule.

In some embodiments, the capsule is formed using materials which include, but are not limited to, natural or synthetic gelatin, pectin, casein, collagen, protein, modified starch, polyvinylpyrrolidone, acrylic polymers, cellulose derivatives, or any combinations thereof. In some embodiments, the capsule is formed using preservatives, coloring and opacifying agents, flavorings and sweeteners, sugars, gastroresistant substances, or any combinations thereof. In some embodiments, the capsule is coated. In some embodiments, the coating covering the capsule includes, but is not limited to, immediate release coatings, protective coatings, enteric or delayed release coatings, sustained release coatings, barrier coatings, seal coatings, or combinations thereof. In some embodiments, a capsule herein is hard or soft. In some embodiments, the capsule is seamless. In some embodiments, the capsule is broken such that the particulates are sprinkled on soft foods and swallowed without chewing. In some embodiments, the shape and size of the capsule also vary. Examples of capsule shapes include, but are not limited to, round, oval, tubular, oblong, twist off, or a non-standard shape. The size of the capsule may vary according to the volume of the particulates. In some embodiments, the size of the capsule is adjusted based on the volume of the particulates and powders. Hard or soft gelatin capsules may be manufactured in accordance with conventional methods as a single body unit comprising the standard capsule shape. A single-body soft gelatin capsule typically may be provided, for example, in sizes from 3 to 22 minims (1 minims being equal to 0.0616 ml) and in shapes of oval, oblong or others. The gelatin capsule may also be manufactured in accordance with conventional methods, for example, as a two-piece hard gelatin capsule, sealed or unsealed, typically in standard shape and various standard sizes, conventionally designated as (000), (00), (0), (1), (2), (3), (4), and (5). The largest number corresponds to the smallest size. In some embodiments, the pharmaceutical composition described herein (e.g., capsule) is swallowed as a whole.

In some embodiments, the capsule comprises one or more pharmaceutically acceptable excipients. In some embodiments, the capsule is free of additional excipients.

Tablet

In some embodiments, the pharmaceutical composition comprising the crystalline composition according to Formula I is formulated as a tablet.

In some embodiments, the tablet size is less than about 1000 mg, less than about 800 mg, less than about 600 mg, less than about 400 mg or less than about 200 mg. In some embodiments, the tablet has a dose strength of more than about 50 mg, more than about 100 mg, more than about 150 mg, more than about 200 mg, or more than about 250 mg. In some embodiments, the tablet size is less than about 1000 mg for a dose strength of more than about 50 mg. In some embodiments, the tablet size is less than 800 mg for a dose strength of more than about 100 mg. In some embodiments, the tablet size is less than 600 mg for a dose strength of more than about 150 mg. In some embodiment, the tablet size is less than 400 mg for a dose strength of more than about 200 mg. In some embodiments, the tablet size is less than 400 mg for a dose strength of 200 mg.

In some embodiments, more than about 20% of the tablet is dissolved in conventional dissolution media. In some embodiments, more than about 40% of the tablet is dissolved in conventional dissolution media. In some embodiments, more than about 50% of the tablet is dissolved in conventional dissolution media. In some embodiments, more than about 60% of the tablet is dissolved in conventional dissolution media. In some embodiments, more than about 70% of the tablet is dissolved in conventional dissolution media. In some embodiments, more than about 80% of the tablet is dissolved in conventional dissolution media. In some embodiments, more than about 20% of the tablet is dissolved in less than 24 hours in conventional dissolution media. In some embodiments, more than about 20% of the tablet is dissolved in less than 12 hours in conventional dissolution media. In some embodiments, more than about 20% of the tablet is dissolved in less than 6 hours in conventional dissolution media. In some embodiments, more than about 20% of the tablet is dissolved in less than 3 hours in conventional dissolution media. In some embodiments, more than about 20% of the tablet is dissolved in less than 2 hours in conventional dissolution media. In some embodiments, more than about 20% of the tablet is dissolved in less than 60 minutes in conventional dissolution media. In some embodiments, more than about 40% of the tablet is dissolved in less than 60 minutes in conventional dissolution media. In some embodiments, more than about 50% of the tablet is dissolved in less than 60 minutes in conventional dissolution media. In some embodiments, more than about 60% of the tablet is dissolved in less than 60 minutes in conventional dissolution media. In some embodiments, more than about 70% of the tablet is dissolved in less than 60 minutes in conventional dissolution media. In some embodiments, more than about 80% of the tablet is dissolved in less than 60 minutes in conventional dissolution media. In some embodiments, more than 70% of the tablet is dissolved in 60 minutes in conventional dissolution media.

In some embodiments, the tablet is produced at a commercial scale.

In some embodiments, the tablet comprises one or more pharmaceutically acceptable excipients.

In some embodiments, the tablet is coated with a coating material, e.g., a sealant. In some embodiments, the coating material is water soluble. In some embodiments, the coating material comprises a polymer, plasticizer, a pigment, or any combination thereof. In some embodiments, the coating material is in the form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of Compound 1. In some embodiments, the coating material is pigmented, clear, or white. In some embodiments, the coating is an enteric coating. Exemplary coating materials include, without limitation, polyvinylpyrrolidone, polyvinyl alcohol, an acrylate-methacrylic acid copolymer, a methacrylate-methacrylic acid copolymer, cellulose acetate phthalate, cellulose acetate succinate, hydroxypropyl methylcellulose phthalate, hydroxypropyl methylcellulose acetate succinate, polyvinyl acetate phthalate, shellac, cellulose acetate trimellitate, sodium alginate, zein, and any combinations thereof.

Oral Dosage Forms

In some embodiments, the pharmaceutical composition comprising the crystalline composition according to Formula I is formulated as an oral dosage form. In some embodiments, the oral dosage form is selected from the group consisting of a tablet, a capsule, a buccal tablet, a sub-lingual table, an orally-disintegrating tablet, a thin film, a liquid solution, a liquid suspension, a syrup, a powder, and solid crystals. In some embodiment, the oral dosage form is selected from the group consisting of a tablet, a capsule, a buccal tablet, a sub-lingual table, an orally-disintegrating tablet, a thin film, a liquid solution, a liquid suspension, a syrup, a powder, solid crystals, minitabs, coated pellets and sachets.

Oral dosage forms may include capsules, tablets, pills, powders or granules. Such forms may include forms that dissolve or disintegrate quickly in the oral environment. Such forms may be prepared with coatings and shells. In some embodiments, these oral dosage forms are capable of controlled or sustained release.

Pharmaceutically Acceptable Excipients

In some embodiments, the pharmaceutical composition comprising the crystalline composition according to Formula I comprises a pharmaceutically acceptable excipient. In some embodiments, the pharmaceutical composition is free of pharmaceutically acceptable excipients. The term "pharmaceutically acceptable excipient", as used herein, means one or more compatible solid or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. In some embodiments, the pharmaceutically acceptable excipient is of sufficiently high purity and sufficiently low toxicity to render them suitable for administration preferably to an animal, preferably mammal, being treated.

Some examples of substances, which can serve as pharmaceutically acceptable excipients include:

Amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, the amino acid is arginine. In some embodiments, the amino acid is L-arginine.

Monosaccharides such as glucose (dextrose), arabinose, mannitol, fructose (levulose), and galactose.

Cellulose and its derivatives such as sodium carboxymethyl cellulose, ethyl cellulose, and methyl cellulose.

Solid lubricants such as talc, stearic acid, magnesium stearate and sodium stearyl fumarate.

Polyols such as propylene glycol, glycerin, sorbitol, mannitol, and polyethylene glycol.

Emulsifiers such as the polysorbates.

Wetting agents such as sodium lauryl sulfate, Tween®, Span, alkyl sulphates, and alkyl ethoxylate sulphates.

Cationic surfactants such as cetrimide, benzalkonium chloride, and cetylpyridinium chloride.

Diluents such as calcium carbonate, microcrystalline cellulose, calcium phosphate, starch, pregelatinized starch, sodium carbonate, mannitol, and lactose.

Binders such as starches (corn starch and potato starch), gelatin, sucrose hydroxypropyl cellulose (HPC), polyvinylpyrrolidone (PVP), and hydroxypropyl methyl cellulose (HPMC).

Disintegrants such as starch, and alginic acid.

Super-disintegrants such as ac-di-sol, croscarmellose sodium, sodium starch glycolate and crospovidone.

Glidants such as silicon dioxide.

Coloring agents such as the FD&C dyes.

Sweeteners and flavoring agents, such as aspartame, saccharin, menthol, peppermint, and fruit flavors.

Preservatives such as benzalkonium chloride, PHMB, chlorobutanol, thimerosal, phenylmercuric, acetate, phenylmercuric nitrate, parabens, and sodium benzoate.

Tonicity adjustors such as sodium chloride, potassium chloride, mannitol, and glycerin.

Antioxidants such as sodium bisulfite, acetone sodium bisulfite, sodium formaldehyde, sulfoxylate, thiourea, and EDTA.

pH adjuster such as NaOH, sodium carbonate, sodium acetate, HCl, and citric acid.

Cryoprotectants such as sodium or potassium phosphates, citric acid, tartaric acid, gelatin, and carbohydrates such as dextrose, mannitol, and dextran.

Surfactants such as sodium lauryl sulfate. For example, cationic surfactants such as cetrimide (including tetradecyl trimethyl ammonium bromide with dodecyl and hexadecyl compounds), benzalkonium chloride, and cetylpyridinium chloride. Some examples of anionic surfactants are alkylsulphates, alkylethoxylate sulphates, soaps, carboxylate ions, sulfate ions, and sulfonate ions. Some examples of non-ionic surfactants are polyoxyethylene derivatives, polyoxypropylene derivatives, polyol derivatives, polyol esters, polyoxyethylene esters, poloxamers, glocol, glycerol esters, sorbitan derivatives, polyethylene glycol (such as PEG-40, PEG-50, or PEG-55) and esters of fatty alcohols.

Organic materials such as carbohydrates, modified carbohydrates, lactose (including a-lactose, monohydrate spray dried lactose or anhydrous lactose), starch, pregelatinized starch, sucrose, mannitol, sorbital, cellulose (including powdered cellulose and microcrystalline cellulose).

Inorganic materials such as calcium phosphates (including anhydrous dibasic calcium phosphate, dibasic calcium phosphate or tribasic calcium phosphate).

Co-processed diluents.

Compression aids.

Anti-tacking agents such as silicon dioxide and talc.

Amounts

In some embodiments, the pharmaceutical composition comprises between about 1 mg and about 500 mg of the crystalline composition according to Formula I. In some embodiments, the pharmaceutical composition comprises between about 1 mg and about 450 mg of the crystalline composition according to Formula I. In some embodiments, the pharmaceutical composition comprises between about 1 mg and about 400 mg of the crystalline composition according to Formula I. In some embodiments, the pharmaceutical composition comprises between about 1 mg and about 350 mg of the crystalline composition according to Formula I. In some embodiments, the pharmaceutical composition comprises between about 1 mg and about 300 mg of the crystalline composition according to Formula I. In some embodiments, the pharmaceutical composition comprises between about 1 mg and about 250 mg of the crystalline composition according to Formula I. In some embodiments, the pharmaceutical composition comprises between about 1 mg and about 200 mg of the crystalline composition according to Formula I. In some embodiments, the pharmaceutical composition comprises between about 1 mg and about 175 mg of the crystalline composition according to Formula I. In some embodiments, the pharmaceutical composition comprises between about 1 mg and about 150 mg of the crystalline composition according to Formula I. In some embodiments, the pharmaceutical composition comprises between about 1 mg and about 125 mg of the crystalline composition according to Formula I. In some embodiments, the pharmaceutical composition comprises between about 1 mg and about 100 mg of the crystalline composition according to Formula I. In some embodiments, the pharmaceutical composition comprises between about 1 mg and about 90 mg of the crystalline composition according to Formula I. In some embodiments, the pharmaceutical composition comprises between about 1 mg and about 80 mg of the crystalline composition according to Formula I. In some embodiments, the pharmaceutical composition comprises between about 1 mg and about 70 mg of the crystalline composition according to Formula I. In some embodiments, the pharmaceutical composition comprises between about 1 mg and about 60 mg of the crystalline composition according to Formula I. In some embodiments, the pharmaceutical composition comprises between about 1 mg and about 50 mg of the crystalline composition according to Formula I. In some embodiments, the pharmaceutical composition comprises between about 1 mg and about 40 mg of the crystalline composition according to Formula I. In some embodiments, the pharmaceutical composition comprises between about 1 mg and about 30 mg of the crystalline composition according to Formula I. In some embodiments, the pharmaceutical composition comprises between about 1 mg and about 20 mg of the crystalline composition according to Formula I. In some embodiments, the pharmaceutical composition comprises between about 1 mg and about 10 mg of the crystalline composition according to Formula I. In some embodiments, the pharmaceutical composition comprises between about 1 mg and about 9 mg of the crystalline composition according to Formula I. In some embodiments, the pharmaceutical composition comprises between about 1 mg and about 8 mg of the crystalline composition according to Formula I. In some embodiments, the pharmaceutical composition comprises between about 1 mg and about 7 mg of the crystalline composition according to Formula I. In some embodiments, the pharmaceutical composition comprises between about 1 mg and about 6 mg of the crystalline composition according to Formula I. In some embodiments, the pharmaceutical composition comprises between about 1 mg and about 5 mg of the crystalline composition according to Formula I. In some embodiments, the pharmaceutical composition comprises between about 1 mg and about 4 mg of the crystalline composition according to Formula I. In some embodiments, the pharmaceutical composition comprises between about 1 mg and about 3 mg of the crystalline composition according to Formula I. In some embodiments, the pharmaceutical composition comprises between about 1 mg and about 2 mg of the crystalline composition according to Formula I.

In some embodiments, the pharmaceutical composition comprises between about 500 mg of the crystalline composition according to Formula I. In some embodiments, the pharmaceutical composition comprises between about 450 mg of the crystalline composition according to Formula I. In some embodiments, the pharmaceutical comprises between about 400 mg of the crystalline composition according to Formula I. In some embodiments, the pharmaceutical composition comprises between about 350 mg of the crystalline composition according to Formula I. In some embodiments, the pharmaceutical composition comprises between about 300 mg of the crystalline composition according to Formula I. In some embodiments, the pharmaceutical composition comprises between about 250 mg of the crystalline composition according to Formula I. In some embodiments, the pharmaceutical composition comprises between about 200 mg of the crystalline composition according to Formula I. In some embodiments, the pharmaceutical composition comprises between about 150 mg of the crystalline composition according to Formula I. In some embodiments, the pharmaceutical composition comprises between about 100 mg of the crystalline composition according to Formula I. In some embodiments, the pharmaceutical composition comprises between about 90 mg of the crystalline composition according to Formula I. In some embodiments, the pharmaceutical composition comprises between about 80 mg of the crystalline composition according to Formula I. In some embodiments, the pharmaceutical composition comprises between about 70 mg of the crystalline composition according to Formula I. In some embodiments, the pharmaceutical composition comprises between about 60 mg of the crystalline composition according to Formula I. In some embodiments, the pharmaceutical composition comprises between about 50 mg of the crystalline composition according to Formula I. In some embodiments, the pharmaceutical composition comprises between about 40 mg of the crystalline composition according to Formula I. In some embodiments, the pharmaceutical composition comprises between about 30 mg of the crystalline composition according to Formula I. In some embodiments, the pharmaceutical composition comprises between about 20 mg of the crystalline composition according to Formula I. In some embodiments, the pharmaceutical composition comprises between about 10 mg of the crystalline composition according to Formula I. In some embodiments, the pharmaceutical composition comprises between about 5 mg of the crystalline composition according to Formula I. In some embodiments, the pharmaceutical composition comprises between about 1 mg of the crystalline composition according to Formula I.

Particle Size

In some embodiments, the pharmaceutical composition comprises the crystalline composition according to Formula I in the form of microparticles. In some embodiments, microparticles of the crystalline composition according to Formula I have an average size from about 1 µm to about 100 µm. In some embodiments, microparticles of the crystalline composition have an average size from about 1 µm to about 90 µm. In some embodiments, microparticles of the crystalline composition have an average size from about 1 µm to about 80 µm. In some embodiments, microparticles of the crystalline composition have an average size from about 1 µm to about 70 µm. In some embodiments, microparticles of the crystalline composition have an average size from about 1 µm to about 60 µm. In some embodiments, microparticles of the crystalline composition have an average size from about 1 µm to about 50 µm. In some embodiments, microparticles of the crystalline composition have an average size from about 1 µm to about 40 µm. In some embodiments, microparticles of the crystalline composition have an average size from about 1 µm to about 30 µm. In some embodiments, microparticles of the crystalline composition have an average size from about 1 µm to about 20 µm. In some embodiments, microparticles of the crystalline composition have an average size from about 1 µm to about 10 µm. In some embodiments, microparticles of the crystalline composition have an average size from about 1 µm to about 5 µm. In some embodiments, microparticles of the crystalline composition have an average size from about 100 µm. In some embodiments, microparticles of the crystalline composition have an average size from about 90 µm. In some embodiments, microparticles of the crystalline composition have an average size from about 80 µm. In some embodiments, microparticles of the crystalline composition have an average size from about 70 µm. In some embodiments, microparticles of the crystalline composition have an average size from about 60 µm. In some embodiments, microparticles of the crystalline composition have an average size from about 50 µm. In some embodiments, microparticles of the crystalline composition have an average size from about 40 µm. In some embodiments, microparticles of the crystalline composition have an average size from about 30 µm. In some embodiments, microparticles of the crystalline composition have an average size from about 20 µm. In some embodiments, microparticles of the crystalline composition have an average size from about 10 µm. In some embodiments, microparticles of the crystalline composition have an average size from about 9 µm. In some embodiments, microparticles of the crystalline composition have an average size from about 8 µm. In some embodiments, microparticles of the crystalline composition have an average size from about 7 µm. In some embodiments, microparticles of the crystalline composition have an average size from about 6 µm. In some embodiments, microparticles of the crystalline composition have an average size from about 5 µm. In some embodiments, microparticles of the crystalline composition have an average size from about 4 µm. In some embodiments, microparticles of the crystalline composition have an average size from about 3 µm. In some embodiments, microparticles of the crystalline composition have an average size from about 2 µm. In some embodiments, microparticles of the crystalline composition have an average size from about 1 µm. In some embodiments, microparticles of the crystalline composition have an average size less than about 100 µm. In some embodiments, microparticles of the crystalline composition have an average size less than about 90 µm. In some embodiments, microparticles of the crystalline composition have an average size less than about 80 µm. In some embodiments, microparticles of the crystalline composition have an average size less than about 70 µm. In some embodiments, microparticles of the crystalline composition have an average size less than about 60 µm. In some embodiments, microparticles of the crystalline composition have an average size less than about 50 µm. In some embodiments, microparticles of the crystalline composition have an average size less than about 40 µm. In some embodiments, microparticles of the crystalline composition have an average size less than about 30 µm. In some embodiments, microparticles of the crystalline composition have an average size less than about 20 µm. In some embodiments, microparticles of the crystalline composition have an average size less than about 10 µm. In some embodiments, microparticles of the crystalline composition have an average size less than about 5 µm.

In some embodiments, the pharmaceutical composition comprising the crystalline composition according to Formula I, wherein the crystalline composition has a D90 from about 1 µm to about 50 µm. In some embodiments, the crystalline composition has a D90 from about 1 µm to about 20 µm, from about 2 µm to about 19 µm, from about 3 µm to about 18 µm, from about 4 µm to about 17 µm, from about 5 µm to about 16 µm, from about 6 µm to about 15 µm, from about 7 µm to about 14 µm, from about 8 µm to about 13 µm, from about 9 µm to about 13 µm, or from about 8 µm to about 12 µm. In some embodiments, the pharmaceutical composition comprising the crystalline composition according to Formula I, wherein the crystalline composition has a D90 of more than about 1 µm, more than about 2 µm, more than about 3 µm, more than about 4 µ, more than about 5 µm, more than about 6 µm, more than about 7 µm, more than about 8 µm, more than about 9 µm, more than about 10 µm, more than about 11 µm, more than about 12 µm, more than about 13 µm, more than about 14 µm more than about 15 µm more than about 16 µm, more than about 17 µm, more than about 18 µm, or more than about 19 µm. In some embodiments, the crystalline composition has a D90 of less than about 20 µm, less than about 19 µm, less than about 18 µm, less than about 17 µm, less than about 16 µm, less than about 15 µm, less than about 14 µm, less than about 13 µm, less than about 12 µm, or less than about 11 µm.

Methods of Preparing the Crystalline Composition According to Formula I

Isolation and purification of the chemical entities and intermediates described herein can be performed, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples below. However, other equivalent separation or isolation procedures can also be used. Prior to crystallization, Compound 1 may be isolated in about 50% chemical purity, 55% chemical purity, 60% chemical purity, 65% chemical purity, 70% chemical purity, 75% chemical purity, 80% chemical purity, 90% chemical purity, 91% chemical purity, 92% purity, 93% chemical purity, 94% chemical purity, 95% chemical purity, 96% chemical purity, 97% chemical purity, 98% chemical purity, 99% chemical purity, about 98% chemical purity, or about 100% chemical purity.

In some embodiments, the crystalline composition according to Formula I disclosed herein are obtained by crystallizing Compound 1 with a chemical purity of less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 78%, less than about 76%, less than about 74%, less than about 72%, or less than about 70%. In some embodiments, the crystalline composition according to Formula I is obtained by crystallizing Compound 1 with a chemical purity in the range of about 70% to about 99%, 80% to about 96%, about 85% to about 96%, about 90% to about 96%, about 80% to 98%, about 85% to about 98%, about 90% to about 98%, about 92% to about 98%, about 94% to about 98%, or about 96% to about 98%.

Preparation of Crystalline Form I

In one aspect, the present disclosure provides a method of preparing a crystalline composition according to Formula I, wherein the method comprises:
(a) dissolving 4-(4-chloro-5-(2,5-dimethyl-7-(pentan-3-yl)pyrazolo[1,5-a]pyrimidin-3-yl)thiazol-2-yl)morpholine (Compound 1) and oxalic acid in a solvent;
(b) heating the solution or slurry from step (a); and
(c) crystallizing the solution or slurry obtained in step (b) to obtain the crystalline composition according to Formula I.

In some embodiments, the solvent in step (a) comprises acetone, heptane, water, 2-butanol, ethyl acetate, 2-propanol, methyl tert-butyl ether, ethanol, methyl ethyl ketone, 1-pentanol, or a combination thereof. In some embodiments, the solvent in step (a) is heptane. In some embodiments, the solvent in step (a) is methyl tert-butyl ether or methyl ethyl ketone. In some embodiments, the solvent in step (a) is a mixture of heptane and methyl ethyl ketone.

In some embodiments, step (b) is heated at about 50° C.

In some embodiments, the concentration of the solution comprising Compound 1 obtained in step (a) is between about 20 mg/mL and about 300 mg/mL. In some embodiments, the concentration of the solution comprising Compound 1 obtained in step (a) is between about 40 mg/mL and about 250 mg/mL. In some embodiments, the concentration of the solution comprising Compound 1 obtained in step (a) is between about 100 mg/mL and about 200 mg/mL. In some embodiments, the concentration of the solution comprising Compound 1 obtained in step (a) is between 125 mg/mL and about 175 mg/mL.

In various embodiments, the method of preparing the crystalline composition according to Formula I involves recrystallization of Compound 1 from a binary, tertiary, or greater solvent system, collectively understood as a multi-solvent system. In some embodiments, the method of preparing the crystalline composition according to Formula I involves crystallization from a mono- or multi-solvent system, where the crystallization involves dissolving Compound 1 in the mono- or multi-solvent system at a temperature above ambient temperature. In some embodiments, the dissolving of Compound 1 in the mono- or multi-solvent system is performed at a temperature of about 0-90° C., 5-90° C., 10-90° C., 15-90° C., 20-90° C., 25-90° C., 30-90° C., 35-90° C., 40-90° C., 45-90° C., 50-90° C., 55-90° C., 60-90° C., 65-90° C., 70-90° C., 75-90° C., 80-90° C., 85-90° C., 0-80° C., 5-80° C., 10-80° C., 20-80° C., 30-80° C., 40-80° C., 50-80° C., 60-80° C., 70-80° C., 0-70° C., 5-70° C., 10-70° C., 15-70° C., 20-70° C., 30-70° C., 40-70° C., 50-70° C., 60-70° C., 0-60° C., 10-60° C., 20-60° C., 30-60° C., 40-60° C., or 50-60° C.

In various embodiments, the crystallization further involves actively heating the solution containing the dissolved Compound 1, for example to a temperature of about 25-100° C., 25-90° C., 25-80° C., 25-70° C., 25-60° C., 25-55° C., 25-50° C., 25-45° C., 25-40° C., 40-100° C., 40-90° C., 40-80° C., 40-70° C., 40-60° C., 40-50° C., 50-100° C., 50-90° C., 50-80° C., 50-70° C., 50-60° C., 60-100° C., 60-90° C., 60-80° C., 60-70° C., 70-100° C., 70-90° C., 70-80° C., 80-100° C., or 80-90° C. In various embodiments, the solution containing the dissolved Compound 1 is maintained at the heated temperature for a period of time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In various embodiments, the crystallization further involves actively cooling the heated solution containing the dissolved Compound 1, for example to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the crystallization further involves actively cooling the heated solution containing the dissolved Compound 1 to a temperature of about 20-30° C. In various embodiments, the solution containing the dissolved Compound 1 is further maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In various embodiments, the steps of active heating followed by active cooling are repeated multiple times, for example at least 2, at least 3, at least 4, at least 5, at least 6, at least 7, at least 8, at least 9, or at least 10 times. In some embodiments, the steps of active heating followed by active cooling are repeated 2, 3, 4, 5, 6, 7, 8, 9, or 10 times.

In various embodiments, the crystallization further involves filtering the solution containing the obtained crystals of the crystalline composition according to Formula I. In some embodiments, the crystallization optionally involves washing the obtained crystals by a solvent, for example by the recrystallization solvent one or more times. In some embodiments, the crystallization optionally involves drying the obtained crystals, for example under vacuum.

In some embodiments, the chemical purity of the crystalline composition according to Formula I is greater than 60%, 70%, 80%, 90%, 95%, or 99%. In some embodiments, the chemical purity of the crystalline composition according to Formula I is greater than about 90%. In some embodiments, the chemical purity of the crystalline composition according to Formula I is greater than about 95%. In some embodiments, the chemical purity of the crystalline composition according to Formula I is greater than about 99%. The chemical purity of the crystalline composition according to Formula I may be measured by any available analytical technique, for example by HPLC analysis.

In various embodiments, the crystalline composition according to Formula I is dry. In various embodiments, the crystalline composition according to Formula I is non-solvated. In various embodiments, the crystalline composition according to Formula I is non-hydrated. In various embodiments, the crystalline composition according to Formula I is anhydrous.

Methods of Treatment

In one aspect, the present disclosure provides a method of treating, preventing, or improving the symptoms of a disease or disorder in a subject in need thereof, comprising administering to the subject a crystalline composition according to Formula I as described herein, or a pharmaceutical composition comprising the crystalline composition according to Formula I as described herein.

In another aspect, the present disclosure provides a method of treating or preventing testicular adrenal rest tumors (TART) or ovarian adrenal rest tumors (OART) in a subject in need thereof, comprising administering to the subject a crystalline composition according to Formula I as described herein, or a pharmaceutical composition comprising the crystalline composition according to Formula I as described herein. In some embodiments, the subject has congenital adrenal hyperplasia (CAH).

In another aspect, the present disclosure provides a method of treating congenital adrenal hyperplasia (CAH) in a subject in need thereof, comprising administering to the subject a crystalline composition according to Formula I as described herein, or a pharmaceutical composition comprising a crystalline composition according to Formula I as described herein. In some embodiments, the CAH is classic CAH. In some embodiments, the CAH is non-classical CAH.

In another aspect, the present disclosure provides a method of improving hyperandrogenic symptoms in a subject in need thereof, comprising administering to the subject a crystalline composition according to Formula I as described herein, or a pharmaceutical composition comprising the crystalline composition according to Formula I as described herein. In some embodiments, the hyperandrongic symptoms are selected from the group consisting of acne, hirsutism, and alopecia.

In another aspect, the present disclosure provides a method of treating menstrual irregularity, ovulatory dysfunction or infertility, in a subject in need thereof, comprising administering to the subject a crystalline composition according to Formula I as described herein, or a pharmaceutical composition comprising the crystalline composition according to Formula I as described herein.

In another aspect, the present disclosure provides a method of improving metabolic symptoms in a subject in need thereof, comprising administering to the subject a crystalline composition according to Formula I as described herein, or the pharmaceutical composition comprising the crystalline composition according to Formula I as described herein. In some embodiments, the metabolic symptoms are selected from the group consisting of body weight, BMI, fat mass, waist circumference, blood pressure and glycemic control.

In another aspect, the present disclosure provides a method of treating polycystic ovary syndrome with functional ovarian hyperandrogenism and functional adrenal hyperandrogenism (PCOS-FOH+FAH) in a subject in need thereof, comprising administering to the subject a crystalline composition according to Formula I as described herein, or the pharmaceutical composition comprising the crystalline composition according to Formula I as described herein.

In another aspect, the present disclosure provides a method of treating polycystic ovary syndrome with functional adrenal hyperandrogenism (PCOS-FAH) in a subject in need thereof, comprising administering to the subject a crystalline composition according to Formula I as described herein, or the pharmaceutical composition comprising the crystalline composition according to Formula I as described herein.

In another aspect, the present disclosure provides a method of treating endometriosis or improving the symptoms of endometriosis in a subject in need thereof, comprising administering to the subject a crystalline composition according to Formula I as described herein, or the pharmaceutical composition comprising the crystalline composition according to Formula I as described herein. In some embodiments, the administration of the crystalline composition or the pharmaceutical composition improves the symptom of pain experienced by the subject. In some embodiments, the administration of the crystalline composition or the pharmaceutical composition reduces the symptoms of pain experienced by the subject. In some embodiments, the administration of the crystalline composition or the pharmaceutical composition prevents the symptom of pain experienced by the subject. In some embodiments, the administration of the crystalline composition or the pharmaceutical composition eliminates the symptom of pain experienced by the subject.

In some embodiments, the methods described herein result in the reduction of a hormone level. Such hormones include deoxycorticosterone, 11-deoxycortisol, Cortisol, corticosterone, aldosterone, pregnenolone, hydroxy pregnenolone, progesterone, 17a-hydroxy progesterone (17-OHP), dehydroepiandrosterone, androstenediol, androstenedione, testosterone, dihydrotestosterone, estrone, estradiol, estriol, and adrenocorticotropic hormone (ACTH). In some embodiments, the methods described herein result in the reduction of 17a-hydroxy progesterone (17-OHP). In some embodiments, the methods described herein result in the reduction of adrenocorticotropic hormone (ACTH), also known as corticotropin.

In various embodiments of the methods as described herein, the crystalline composition or the pharmaceutical composition is administered at a dose from about 5 mg/day to about 1000 mg/day. In some embodiments, the crystalline composition or the pharmaceutical composition is administered in a fed state. In some embodiments, the crystalline composition or the pharmaceutical composition is administered in a fasted state. In some embodiments, the crystalline composition or the pharmaceutical composition is administered at least once per day.

In some embodiments of the methods described herein, the crystalline composition or the pharmaceutical composition is administered at bedtime. In some embodiments, the methods described herein include administration of the crystalline composition or the pharmaceutical compositions described herein less than about 4 hours before sleep. In some embodiments, the methods described herein include administration of the crystalline composition or the pharmaceutical compositions described herein less than about 3 hours before sleep. In some embodiments, the methods described herein include administration of the crystalline composition or the pharmaceutical compositions described herein less than about 2 hours before sleep. In some embodiments, the methods described herein include administration of the crystalline composition or the pharmaceutical compositions described herein less than about 1 hour before sleep. In some embodiments, the methods described herein include administration of the crystalline composition or the pharmaceutical compositions described herein less than about 30 mins before sleep.

In some embodiments, the methods described herein include administration of the crystalline composition or the pharmaceutical compositions described herein at or before the expected circadian release of adrenocorticotropic hormone (ACTH). In some embodiments, the methods described herein include administration of the crystalline composition or the pharmaceutical compositions described herein about 3-4 hours before the expected circadian release of adrenocorticotropic hormone (ACTH).

In various embodiments of the methods as described herein, the method further comprises administering to the subject an additional chemotherapeutic agent. In some embodiments, the additional chemotherapeutic agent is glucocorticoid, a mineralocorticoid, an ACAT1 inhibitor, or an anti-androgen agent. In some embodiments, the glucocorticoid is beclomethasone, betamethasone, budesonide, cortisone, dexamethasone, hydrocortisone, methylprednisolone, prednisolone, prednisone, or triamcinolone. In some embodiments, the mineralocorticoid is fludrocortisone. In some embodiments, the additional chemotherapeutic agent is another CRF1antagonist.

In various embodiments of the methods as described herein, the method further comprises an additional treatment selected from surgical resection of the tumors and radiation therapy, or a combination thereof. In some embodiments, the additional therapy is surgical resection and the surgical resection is prior to, after, and/or concurrent with administration of the crystalline composition as described herein, or the pharmaceutical composition comprising the crystalline composition as described herein. In some embodiments, the additional therapy is radiation therapy and the radiation therapy is prior to, after, and/or concurrent with administration of the crystalline composition as described herein, or the pharmaceutical composition comprising the crystalline composition as described herein.

In various embodiments of the methods, the subject is from about 9 years of age to about 18 years of age. In some embodiments, the subject is from about 8 years of age to about 55 years of age.

EXAMPLES

The following examples serve to further describe the manner of using the present disclosure. These examples are presented for illustrative purpose and should not serve to limit the true scope of the present disclosure.

In carrying out the procedures of the methods described herein, it is of course to be understood that references to particular buffers, media, reagents, cells, culture conditions, and the like are not intended to be limiting, but are to be read so as to include all related materials that one of ordinary skill in the art would recognize as being of interest or value in the particular context in which that discussion is presented. For example, it is often possible to substitute on buffer system or culture medium for another and still achieve similar, if not identical, results. Those of skill in the art will have sufficient knowledge of such systems and methodologies so as to able, without undue experimentation, to make such substitutions as will optimally serve their purposes in using the methods and procedures disclosed herein.

Example 1—Preparation and Characterization of the Crystalline Composition According to Formula I Preparation of the Crystalline Composition According to Formula I A mixture of 185.0 mg (0.441 mmol) of 4-(4-chloro-5-(2,5-dimethyl-7-(pentan-3-yl)pyrazolo[1,5-a]pyrimidin-3-yl)thiazol-2-yl)morpholine (Compound 1), 45.0 mg (0.500 mmol) of oxalic acid, and 2.5 mL of diisopropyl ether was agitated. After one hour, an additional 1 mL of diisopropyl ether was added. After stirring overnight, the mixture was vacuum filtered and the resulting solid was dried to afford 170 mg (76%) of the crystalline composition according to Formula I as solid.

X-Ray Powder Diffraction

X-ray powder diffraction (XPRD) patterns were obtained on a Rigaku Smart-Lab X-ray diffraction system. A CuK source (=0.71073 Å) operating minimally at 40 kV and 44 mA scans each sample between 2 and 40 degrees 2θ. The step size is 0.02 °2θ.

The XRPD pattern obtained for the crystalline composition according to Formula I is summarized in Table 1 below and shown in FIG. 1.

TABLE 1

XRPD Data of the Crystalline Composition according to Formula 1

| Peak # | Angle (° 2-θ) | Intensity (%) |
|---|---|---|
| 1 | 5.44 | 31 |
| 2 | 8.82 | 12 |
| 3 | 10.84 | 100 |
| 4 | 11.70 | 12 |
| 5 | 14.60 | 8 |
| 6 | 15.56 | 6 |
| 7 | 15.96 | 52 |
| 8 | 16.28 | 5 |
| 9 | 16.70 | 10 |
| 10 | 17.66 | 4 |
| 11 | 18.44 | 5 |
| 12 | 18.82 | 6 |
| 13 | 19.18 | 8 |
| 14 | 19.60 | 2 |
| 15 | 20.02 | 11 |
| 16 | 20.50 | 11 |
| 17 | 20.78 | 20 |
| 18 | 21.72 | 7 |
| 19 | 22.12 | 2 |
| 20 | 22.74 | 18 |
| 21 | 23.04 | 16 |
| 22 | 23.44 | 31 |
| 23 | 24.80 | 48 |
| 24 | 25.52 | 6 |
| 25 | 25.92 | 9 |
| 26 | 26.58 | 4 |
| 27 | 26.80 | 14 |
| 28 | 26.94 | 8 |
| 29 | 27.62 | 3 |
| 30 | 28.00 | 13 |
| 31 | 28.86 | 14 |
| 32 | 29.54 | 3 |
| 33 | 31.26 | 3 |
| 34 | 31.66 | 5 |
| 35 | 31.88 | 4 |
| 36 | 32.16 | 3 |
| 37 | 32.48 | 2 |
| 38 | 32.86 | 5 |
| 39 | 33.46 | 2 |
| 40 | 34.36 | 2 |
| 41 | 35.02 | 3 |
| 42 | 35.44 | 1 |
| 43 | 35.98 | 2 |
| 44 | 36.72 | 4 |
| 45 | 37.04 | 3 |
| 46 | 37.80 | 5 |
| 47 | 38.28 | 2 |
| 48 | 38.90 | 2 |
| 49 | 39.20 | 2 |

Differential Scanning Calorimetry (DSC)

Differential scanning calorimetry analysis was carried out on a TA Instruments Q2500 Discovery Series instrument. The instrument temperature calibration was performed using indium. The DSC cell was kept under a nitrogen purge of about 50 mL per minute during each analysis. The sample was placed in a standard, crimpled, aluminum pan and was heated from approximately 25° C. to 350° C. at a rate of 10° C. per minute. The DSC trace of the crystalline composition according to Formula I is shown in FIG. 2.

Thermogravimetric Analysis (TGA)

Thermogravimetry analyses were carried out using a TA Instruments Discovery TGA 5500 instrument that was cooled using a TA Instruments Refrigerated Cooling System (RCS) 90 chiller. The instrument balance was calibrated using class M weights and temperature calibration was performed by measurement of the Curie point of Alumel®. Sample was loaded onto a platinum sample pan and the pan was loaded into the TG instrument. The pan was heated from ambient temperature to 350° C. at a rate of 10° C. per minute. The instrument was controlled using TA Trios software. The TGA trace of the crystalline composition according to Formula I is shown in FIG. 3.

Dynamic Vapor Sorption (DVS)

The DVS analysis was carried out on a TA Instruments Q5000 sorption analyzer. The instrument was calibrated with standard weights and a sodium bromide standard for humidity. For each analysis, a portion of the sample was weighed into a metal-coated, quartz pan. Each sample was analyzed at 25° C. with a maximum equilibration time of 60 minutes in 10% relative humidity (RH) steps from 5 to 95% RH (adsorption cycle) and from 95 to 5% RH (desorption cycle). Data collection was performed using Advantage for Q Series version 5.5.23. The percent weight change values were calculated using Microsoft Excel®. The DVS trace of the crystalline composition according to Formula I is shown in FIG. 4.

Infrared (IR)

The IR spectrum was obtained using a Nicolet iS50 Model 60825 Fourier-transform (FT) IR spectrophotometer equipped with a deuterated triglycine sulfate (DTGS) detector, a potassium bromide (KBr) beamsplitter, and an electronically temperature controlled (ETC) Ever-Glo® IR source. The instrument was configured with a SMART iTR diamond attenuated total reflectance (ATR) sampling accessory. The single beam scan of the background (air) and sample were collected with 128 signal-averaged scans at a resolution of 2 cm-1 over the spectral range 400-4000 cm-1. The wavelength calibration was verified using a certified polystyrene standard. Data collection and processing was performed using Omnic 9.2 software. The IR spectrum of the crystalline composition according to Formula I is shown in FIG. 5.

Proton Nuclear Magnetic Resonance ($^1$H NMR)

The 1H NMR spectrum was acquired on a Bruker Avance 400 MHz spectrometer using TopSpin v3.2 software. The sample was dissolved in CD3OD and the resulting solution was transferred into a 5-mm NMR tube for subsequent data acquisition. Data collection parameters are shown in Table 14. The spectrum was processed using the program MNova and referenced to the chemical shift of the residual protons in CD3OD (3.31 ppm). The $^1$H NMR spectrum of the crystalline composition according to Formula I is shown in FIG. 6.

Raman

The Raman spectrum was acquired utilizing a Thermo Scientific model iS50 Fourier-transform (FT) IR spectrophotometer equipped with a Raman accessory. The system is equipped with an indium gallium arsenide (InGaAs) detector, a calcium fluoride (CaF2) beamsplitter, and a 2.5 W laser operating at 1064 nm. The module was conFIG.d with a 180° reflective sampling accessory. A sample was prepared by loading particles onto a glass slide. Each FT-Raman spectrum was collected using 0.50 W laser power with 256 signal-averaged scans at a resolution of 4 cm-1 over the spectral range 100-3700 cm-1. The wavelength calibration was verified using a polystyrene. Data acquisition and processing were performed using Omnic 9.7 software. The Raman spectrum of the crystalline composition according to Formula I is shown in FIG. 7.

The invention claimed is:

1. A crystalline composition comprising:
Compound 1:

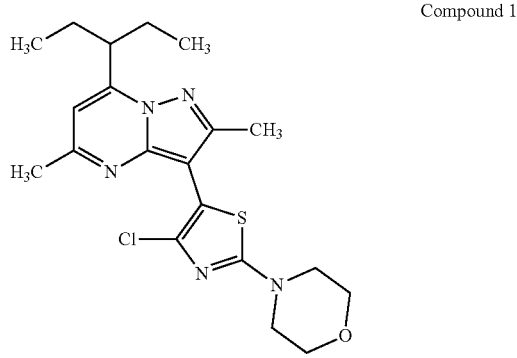 [SMILES: CCC(CC)c1cc(C)nc2c(-c3sc(N4CCOCC4)nc3Cl)c(C)nn12]

Compound 1 at T=150° K. of: a=34.003(4) Å, b=6.5843(13) Åc=21.062(5) Å; β=108.703(12)°, V=4466.5(15) Å³ and a monoclinic C2/c space group.

2. The crystalline composition of claim 1, wherein the crystalline composition is characterized by an X-ray powder diffraction pattern comprising peaks at 10.84±0.2° 2-θ, 15.96±0.2° 2-θ, 23.44±0.2° 2-θ, and 24.80±0.2° 2-θ, and as measured by X-ray powder diffraction using an X-ray wavelength of 0.71073 Å.

3. The crystalline composition of claim 2, wherein the X-ray powder diffraction pattern further comprising at least one peak selected from 5.44±0.2° 2-θ, 20.78±0.2° 2-θ, 22.74±0.2° 2-θ, 23.04±0.2° 2-θ, 26.80±0.2° 2-θ, and 28.86±0.2° 2-θ, and as measured by X-ray powder diffraction using an X-ray wavelength of 0.71073 Å.

4. The crystalline composition of claim 3, wherein the X-ray powder diffraction pattern further comprising at least five peaks selected from 8.82±0.2° 2-θ, 11.70±0.2° 2-θ, 14.60±0.2° 2-θ, 15.56±0.2° 2-θ, 16.70±0.2° 2-θ, 18.82±0.2° 2-θ, 19.18±0.2° 2-θ, 20.02±0.2° 2-θ, 20.50±0.2° 2-θ, 21.72±0.2° 2-θ, 25.52±0.2° 2-θ, 25.92±0.2° 2-θ, 26.94±0.2° 2-θ, and 28.00±0.2° 2-θ, and as measured by X-ray powder diffraction using an X-ray wavelength of 0.71073 Å.

5. The crystalline composition of claim 3, wherein the X ray powder diffraction pattern further comprises a peak at 5.44±0.2° 2-θ.

6. The crystalline composition of claim 1, wherein the crystalline composition is characterized by a differential scanning calorimetry (DSC) thermogram comprising an endotherm in the range of about 160° C. to 170° C.

7. The crystalline composition of claim 1, wherein the crystalline composition is characterized by a differential scanning calorimetry (DSC) thermogram comprising an endotherm with an onset of about 164° C. and a peak of about 166° C.

8. The crystalline composition of claim 1, wherein the crystalline composition is characterized by a melting point of about 166° C.

9. The crystalline composition of claim 1, wherein the crystalline composition is characterized by a thermogravimetric analysis (TGA) thermogram comprising a loss in mass of about 11% over a temperature range of about 25° C. to about 200° C.

10. The crystalline composition of claim 1, wherein the crystalline composition is characterized by:
(a) an X-ray powder diffraction pattern comprising peaks at 10.84±0.2° 2-θ, 15.96±0.2° 2-θ, 23.44±0.2° 2-θ, and 24.80±0.2° 2-θ, and as measured by X-ray powder diffraction using an X-ray wavelength of 0.71073 Å;
(b) a differential scanning calorimetry (DSC) thermogram comprising an endotherm in the range of about 160° C. to 170° C.;
(c) a differential scanning calorimetry (DSC) thermogram comprising an endotherm with an onset of about 164° C. and a peak of about 166° C.;
(d) a thermogravimetric analysis (TGA) thermogram comprising a loss in mass of about 11% over a temperature range of about 25° C. to about 200° C.; or
(e) combinations thereof.

11. A pharmaceutical composition comprising a crystalline composition comprising
Compound 1:

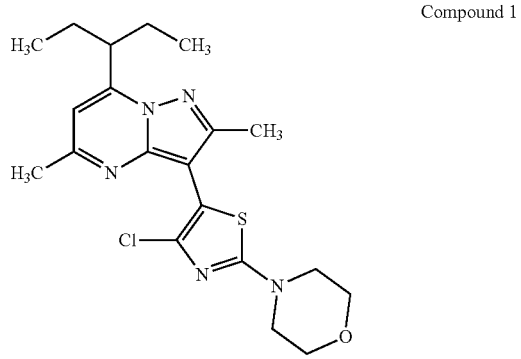 [SMILES: CCC(CC)c1cc(C)nc2c(-c3sc(N4CCOCC4)nc3Cl)c(C)nn12]

Compound 1 at T=150° K. of: a=34.003(4) Å, b=6.5843(13) Åc=21.062(5) Å; β=108.703(12)°, V=4466.5(15) Å³ and a monoclinic C2/c space group.

12. The pharmaceutical composition of claim 11, wherein the pharmaceutical composition comprises between about 1 mg and about 500 mg of the crystalline composition comprising Compound I and oxalic acid.

* * * * *

UNITED STATES PATENT AND TRADEMARK OFFICE
CERTIFICATE OF CORRECTION

PATENT NO. : 11,708,372 B2
APPLICATION NO. : 17/720074
DATED : July 25, 2023
INVENTOR(S) : Dasharatha Reddy et al.

Page 1 of 1

It is certified that error appears in the above-identified patent and that said Letters Patent is hereby corrected as shown below:

In the Claims

Column 33, Line 29, Claim 1:
Add "and oxalic acid in a molar ratio of 2:1 of Compound 1 to oxalic acid, wherein the crystals have unit cell parameters"

Column 34, Line 49, Claim 11:
Add "and oxalic acid in a molar ratio of 2:1 of Compound 1 to oxalic acid, wherein the crystals have unit cell parameters"

Signed and Sealed this
Twenty-sixth Day of September, 2023

Katherine Kelly Vidal
*Director of the United States Patent and Trademark Office*